United States Patent

Ishikawa et al.

[11] Patent Number: 5,362,736
[45] Date of Patent: Nov. 8, 1994

[54] ISOQUINOLINE DERIVATIVES

[75] Inventors: Kiyofumi Ishikawa, Chofu; Takashi Hayama, Kawasaki; Masaru Nishikibe, Urayasu; Mitsuo Yano, Yokohama, all of Japan

[73] Assignee: Banyu Pharmaceutical Co., Ltd., Tokyo, Japan

[21] Appl. No.: 840,847

[22] Filed: Feb. 25, 1992

Related U.S. Application Data

[63] Continuation-in-part of Ser. No. 834,621, Feb. 12, 1992, abandoned.

[30] Foreign Application Priority Data

Feb. 27, 1991 [JP] Japan .................. 3-055915

[51] Int. Cl.$^5$ .................. C07D 491/00; A01N 43/42
[52] U.S. Cl. .................. 514/291; 514/307; 546/90; 546/141; 546/143; 546/147
[58] Field of Search .......... 546/90, 141, 143, 146, 546/147; 514/291, 307

[56] References Cited

U.S. PATENT DOCUMENTS

| | | | |
|---|---|---|---|
| 4,613,606 | 9/1986 | Clark et al. | 514/307 |
| 4,851,537 | 7/1989 | Noyori et al. | 546/146 |
| 4,963,563 | 10/1990 | Franzmann et al. | 546/141 |
| 4,963,684 | 10/1990 | Morita et al. | 546/90 |

FOREIGN PATENT DOCUMENTS 9002119  3/1990  WIPO .

OTHER PUBLICATIONS

Chemical Abstracts, vol. 61, No. 2 Jul. 20, 1964, Col. 1829c–1830d, Columbus, Ohio, US; I. Kazuyoshi et al.: "Influence . . . Synthesis".

*Primary Examiner*—C. Warren Ivy
*Assistant Examiner*—Raymond Covington
*Attorney, Agent, or Firm*—Ladas & Parry

[57] ABSTRACT

Novel isoquinoline derivatives represented by formula (I):

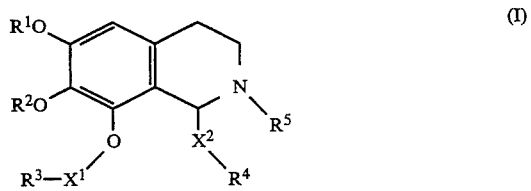

wherein $R^1$, $R^2$, $R^3$, $R^4$, $R^5$, $X^1$ and $X^2$ are as defined in the specification, have an anti-arrhythmic activity and bradycardiac activity and are effective for the treatment of arrhythmia, myocardial infarction or angina pectoris.

4 Claims, No Drawings

ISOQUINOLINE DERIVATIVES

This application is a continuation in part of application Ser. No. 07/834,621 filed 12 Feb. 1992, now abandoned.

BACKGROUND OF THE INVENTION

1. Field of the Invention

The present invention relates to new isoquinoline derivatives having an anti-arrhythmic activity and bradycardiac activity and their medical use. The compounds of the present invention can be utilized as therapeutic agents in the medical field, especially, as agents for the treatment of arrhythmia, myocardiac infarction or angina pectoris.

2. Statement of the Related Art

As compounds having a selective bradycardiac activity, there are known alinidine, benzazepine derivatives (UL-FS49) [cf., Drugs of the Future, 10, 639 (1985)]. However, it has not been reported that isoquinoline derivatives analogous to the compounds of the present invention would have a bradycardiac activity and anti-arrhythimic activity.

Currently, heart diseases have been a serious problem as clinical causes for death. It has thus been desired to develop an excellent agent for the treatment of heart diseases.

SUMMARY OF THE INVENTION

Accordingly, an object of the present invention is to provide a new isoquinoline derivative having an anti-arrhythimic activity and bradycardiac activity without adversely affecting blood pressure which is useful for the treatment of heart diseases, particularly, arrhythmia, myocardiac infarction or angina pectoris.

Another object of the present invention is to provide a medical use of the isoquinoline derivative.

According to the present invention, there are provided with a compound represented by general formula (I):

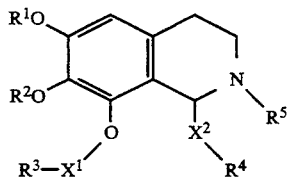

wherein
each of $R^1$ and $R^2$ independently represents a lower alkyl group or both are combined together to form a methylene group;

$X^1$ represents a divalent alkylene chain having 1 to 5 carbon atoms which may be substituted with a lower alkyl group (one optional methylene group in which alkylene chain may be replaced by one group selected from the group consisting of an oxy group, a thio group, a sulfinyl group, a sulfonyl group or a group shown by formula: —$NR^6$— wherein $R^6$ represents a hydrogen atom or a lower alkyl group); provided that the said methylene group is not the methylene group adjacent to the oxygen atom at the 8-position of the isoquinoline ring;

$X^2$ represents a divalent alkylene chain having 1 to 4 carbon atoms which may be substituted with a lower alkyl group;

each of $R^3$ and $R^4$ represents independently an aryl group or a heteroaryl group, each of which groups may be substituted with 1 to 3 substituents, which may be the same or different and are selected from the group consisting of a lower alkyl group, a lower alkoxy group, a methylenedioxy group, a halogen atom, a nitro group, a hydroxy group, a cyano group, a lower alkoxycarbonyl group, a lower alkanoyl group, an amino group, an N-mono-lower alkylamino group, an N,N-di-lower alkylamino group, a carbamoyl group, an N-mono-lower alkylcarbamoyl group, an N,N-di-lower alkylcarbamoyl group, an amino-lower alkyl group, an N-mono-lower alkylamino-lower alkyl group, an N,N-di-lower alkylamino-lower alkyl group, an N-(hydroxy-lower alkyl)amino-lower alkyl group, an N-lower-alkyl-N-(hydroxy-lower alkyl)amino-lower alkyl group, an N,N-di(hydroxy-lower alkyl)amino-lower alkyl group, an N-(lower alkoxy-lower alkyl)amino-lower alkyl group, an N-lower alkyl-N-(lower alkoxy-lower alkyl)amino-lower alkyl group, an N,N-di(lower alkoxy-lower alkyl)amino-lower alkyl group and a nitrogen-containing saturated heterocyclic lower alkyl group; and $R^5$ represents a lower alkoxycarbonyl group, a lower alkylsulfonyl group, a group shown by formula:

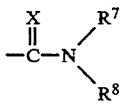

wherein each of $R^7$ and $R^8$ independently represents a hydrogen atom or a lower alkyl group which may be substituted with 1 or 2 substituents, which may be the same or different and are selected from the group consisting of a hydroxy group and a lower alkoxy group, or both are combined together with the nitrogen atom adjacent thereto to form a saturated nitrogen-containing heterocyclic group; and X represents an oxygen atom or a sulfur atom; or a lower alkanoyl group which may be substituted with 1 or 2 substituents, which may be the same or different and are selected from the group consisting of a lower alkylsulfinyl group, a group shown by formula: $R^9S$— wherein $R^9$ represents a hydrogen atom, a lower alkyl group, a lower alkanoyl group, a carbamoyl group, an N-mono-lower alkylcarbamoyl group, an N,N-di-lower alkylcarbamoyl group or a lower alkoxycarbonyl group; a group shown by formula: $R^{10}O$— wherein $R^{10}$ represents a hydrogen atom, a lower alkyl group or a lower alkanoyl group which may be substituted with a hydroxy group; and a group shown by formula:

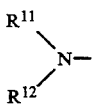

wherein each $R^{11}$ and $R^{12}$ independently represents a hydrogen atom, a lower alkyl group or a lower alkanoyl group, or both are combined together to form a 5- to 7-membered nitrogen-containing saturated heterocyclic ring having 3 to 6 carbon atoms together with the nitrogen atom adjacent thereto, wherein one methylene group not adjacent to the nitrogen atom for forming the ring may be replaced by an oxy group or a thio group and one methylene group adjacent to the nitrogen atom may be replaced by a carbonyl group, and a pharmaceutically acceptable salt thereof.

DETAILED DESCRIPTION OF PREFERRED EMBODIMENTS

Various terms referred to throughout the specification and embraced in the scope of the invention are defined below and specific examples are also given below.

The term "lower" is used to mean that the group or compound expressed by the term has carbon atoms of 6 or less, unless otherwise indicated. Therefore, the term "lower alkyl group" refers to a straight or branched alkyl group having 1 to 6 carbon atoms. Specific examples of the lower alkyl group include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

Examples of the "lower alkoxy group" include methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy and isohexyloxy.

Examples of the "aryl group" include phenyl and naphthyl.

The term "heteroaryl group" is used to mean a monocyclic heteroaryl group containing hetero atom(s) such as an oxygen atom, a sulfur atom and a nitrogen atom. Examples of the heteroaryl group include pyridyl, furyl, thienyl, pyrrolyl and thiazolyl.

Examples of the "halogen atom" include a fluorine atom, a chlorine atom, a bromine atom and an iodine atom.

Examples of the "lower alkoxycarbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and pentyloxycarbonyl.

Examples of the "lower alkanoyl group" include formyl, acetyl, propionyl, butyryl, valeryl, pivaloyl and hexanoyl.

The term "N-mono-lower alkylamino group" is used to mean an amino group substituted with one lower alkyl group defined as described above and specific examples include N-methylamino, N-ethylamino, N-propylamino, N-isopropylamino and N-butylamino.

The term "N,N-di-lower alkylamino group" is used to mean an amino group substituted with two lower alkyl groups defined as described above which may be the same or different. Specific examples include N,N-dimethylamino, N-ethyl-N-methylamino, N,N-diethylamino, N-ethyl-N-propylamino, N,N-dipropylamino and N,N-dibutylamino.

The term "N-mono-lower alkylcarbamoyl group" is used to mean a carbamoyl group substituted with one lower alkyl group defined as described above. Specific examples include N-methylcarbamoyl, N-ethylcarbamoyl, N-propylcarbamoyl and N-butylcarbamoyl.

The term "N,N-di-lower alkylcarbamoyl group" is used to mean a carbamoyl group substituted with two lower alkyl groups defined as above which may be the same or different. Specific examples include N,N-dimethylcarbamoyl, N-ethyl-N-methylcarbamoyl, N,N-diethylcarbamoyl and N-ethyl-N-propylcarbamoyl.

The term "amino-lower alkyl group" is used to mean a lower alkyl group defined above which is substituted with an amino group. Specific examples include aminomethyl, 1-aminoethyl, 2-aminoethyl, 1-aminopropyl, 2-aminopropyl, 3-aminopropyl, 1-amino-1-methylethyl, 2-amino-1-methylethyl, 1-aminobutyl, 2-aminobutyl, 3-aminobutyl and 4-aminobutyl.

The term "N-mono-lower alkylamino-lower alkyl group" is used to mean a lower alkyl group as defined above which is substituted with the N-mono-lower alkylamino group defined above. Specific examples include N-methylaminomethyl, 1-(N-methylamino)ethyl, 2-(N-methylamino)ethyl, 1-(N-methylamino)propyl, 2-(N-methylamino)propyl, 3-(N-methylamino)propyl, N-ethylaminomethyl, 1-(N-ethylamino)ethyl, 2-(N-ethylamino)ethyl, 1-(N-ethylamino)propyl, N-propylaminomethyl and N-isopropylaminomethyl.

The term "N,N-di-lower alkylamino-lower alkyl group" is used to mean a lower alkyl group as defined above which is substituted with the N,N-di-lower alkylamino group as described above. Specific examples include N,N-dimethylaminomethyl, 1-(N,N-dimethylamino)ethyl, 2-(N,N-dimethylamino)ethyl, 1-(N,N-dimethylamino)propyl, 2-(N,N-dimethylamino)propyl, 3-(N,N-dimethylamino)propyl, N-ethyl-N-methylaminomethyl, 1-(N-ethyl-N-methylamino)ethyl, 2-(N-ethyl-N-methylamino)ethyl, N,N-diethylaminomethyl, 1-(N,N-diethylamino)ethyl, 2-(N,N-diethylamino)ethyl, N-ethyl-N-propylaminomethyl, N,N-dipropylaminomethyl and N,N-diisopropylaminomethyl.

The term "hydroxy-lower alkyl group" is used to mean a lower alkyl group defined as above which is substituted with one hydroxy group at the position other than 1-position thereof. Specific examples include 2-hydroxyethyl, 2-hydroxypropyl and 3-hydroxypropyl.

The term "N-(hydroxy-lower alkyl)amino-lower alkyl group" is used to mean a lower alkyl group as defined above which has an amino group substituted with one hydroxy-lower alkyl group as defined above. Specific examples include N-(2-hydroxyethyl)aminomethyl, 1-(N-(2-hydroxyethyl)amino)ethyl, 2-(N-(2-hydroxyethyl)amino)ethyl, N-(2-hydroxypropyl)aminomethyl and N-(3-hydroxypropyl)aminomethyl.

The term "N-lower alkyl-N-(hydroxy-lower alkyl)amino-lower alkyl group" is used to mean a lower alkyl group as defined above which contains an amino group substituted with the lower alkyl group defined as above and the hydroxy-lower alkyl group defined as above. Specific examples include N-(2-hydroxyethyl)-N-methylaminomethyl, 1-(N-(2-hydroxyethyl)-N-methylamino)ethyl, 2-(N-(2-hydroxyethyl)-N-methylamino)ethyl, and 3-(N-(2-hydroxyethyl)-N-methylamino)propyl.

The term "N,N-di(hydroxy-lower alkyl)amino-lower alkyl group" is used to mean a lower alkyl group as defined above which contains an amino group substituted with the two hydroxy-lower alkyl groups defined above which may be the same or different. Specific examples include N,N-di(2-hydroxyethyl)aminomethyl, 2-(N,N-di(2-hydroxyethyl)amino)ethyl, 3-(N,N-di(2-hydroxyethyl)amino)propyl and N-2-hydroxyethyl-N-3-hydroxypropylaminomethyl.

The term "lower alkoxy-lower alkyl group" is used to mean a lower alkyl group as defined above in which the hydrogen atom other than the 1-position is replaced by one lower alkoxy group as defined above. Specific examples include 2-methoxyethyl, 2-methoxypropyl and 3-methoxypropyl.

The term "N-(lower alkoxy-lower alkyl)amino-lower alkyl group" is used to mean a lower alkyl group as defined above which contains an amino group substituted with one lower alkoxy-lower alkyl group defined as described above. Specific examples include N-(2-methoxyethyl)aminomethyl, 1-(N-(2-methoxyethyl)amino)ethyl, 2-(N-(2-methoxyethyl)amino)ethyl, N-(3-methoxypropyl)aminomethyl and N-(2-ethoxyethyl)aminomethyl.

The term "N-lower alkyl-N-(lower alkoxy-lower alkyl)amino-lower alkyl group" is used to mean a lower alkyl group as defined above which contains an amino group substituted with the lower alkyl group defined above and the lower alkoxy-lower alkyl group defined above. Specific examples include N-(2-methoxyethyl)-N-methylaminomethyl, 1-(N-(2-methoxyethyl)-N-methylamino)ethyl, 2-(N-(2-methoxyethyl)-N-methylamino)ethyl and N-ethyl-N-(2-methoxyethyl)aminomethyl.

The term "N,N-di(lower alkoxy-lower alkyl) amino-lower alkyl group" is used to mean a lower alkyl group as defined above which contains an amino group substituted with two lower alkoxy-lower alkyl groups defined above which may be the same or different. Specific examples include N,N-di(2-methoxyethyl)aminomethyl, 2-(N,N-di(2-methoxyethyl)aminoethyl, 3-(N,N-di(2-methoxyethyl)aminopropyl and N-(2-methoxyethyl)-N-(3-methoxypropyl)aminomethyl.

The term "nitrogen-containing saturated heterocyclic lower alkyl group" is used to mean a lower alkyl group as defined above which contains a 5- to 9-membered saturated heterocyclic ring having 3 to 8 carbon atoms which has at least one nitrogen atom in the ring thereof and the methylene group not adjacent to the nitrogen atom may be replaced by oxy, thio, sulfinyl or sulfonyl. Specific examples include pyrrolidinomethyl, pyrrolidin-2-ylmethyl, N-methylpyrrolidin-2-ylmethyl, 1-pyrrolidinoethyl, 2-pyrrolidinoethyl, 2-(pyrrolidin-2-yl)ethyl, 2-(N-methylpyrrolidin-2-yl)ethyl, 1,3-thiazolidin-3-ylmethyl, 1,3-thiazolidin-2-ylmethyl, N-methyl-1,3-thiazolidin-2-ylmethyl, 1-(1,3-thiazolidin-3-yl)ethyl, 2-(1,3-thiazolidin-3-yl)ethyl, 2-(N-methyl-1,3-thiazolidin-2-yl)ethyl, piperidinomethyl, piperidin-2-ylmethyl, N-methylpiperidin-2-ylmethyl, 1-piperidinoethyl, 2-piperidinoethyl, 2-(piperidin-2-yl)ethyl, 2-(N-methylpiperidin-2-yl)ethyl, morpholinomethyl, morpholin-3-ylmethyl, N-methylmorpholin-3-ylmethyl, 1-morpholinoethyl, 2-morpholinoethyl, 2-(morpholin-3-yl)ethyl, 2-(N-methylmorpholin-3-yl)ethyl, perhydro-1,4-thiazin-4-ylmethyl, perhydro-1,4-thiazin-3-ylmethyl, perhydro-N-methyl-1,4-thiazin-3-ylmethyl, 1-(perhydro-1,4-thiazin-4-yl)ethyl, 2-(perhydro-1,4-thiazin-4-yl)ethyl, 2-(perhydro-1,4-thiazin-3-yl)ethyl, 2-(perhydro-N-methyl-1,4-thiazin-3-yl)ethyl, perhydro-1,4-thiazin-1-oxid-4-ylmethyl, perhydro-1,4-thiazin-1-oxid-3-ylmethyl, perhydro-N-methyl-1,4-thiazin-1-oxid-3-ylmethyl, 1-(perhydro-1,4-thiazin-1-oxid-4-yl)ethyl, 2-(perhydro-1,4-thiazin-1-oxid-4-yl)ethyl, perhydro-1,4-thiazin-1,1-dioxid-4-ylmethyl, 2-(perhydro-1,4-thiazin-1,1-dioxid-4-yl)ethyl, piperazin-1-ylmethyl, 2-(piperazin-1-yl)ethyl, N-methylpiperazin-1-ylmethyl, 2-(N-methylpiperazin-1-yl)ethyl, N,N'-dimethylpiperazin-2-ylmethyl, 2-(N,N'-dimethylpiperazin-2-yl)ethyl, perhydroazepin-1-ylmethyl, 1-(perhydroazepin-1-yl)ethyl, perhydroazocin-1-ylmethyl and perhydroazonin-1-ylmethyl.

Examples of the "lower alkylsulfonyl group" include mesyl, ethylsulfonyl, propylsulfonyl, isopropylsulfonyl, butylsulfonyl, isobutylsulfonyl, sec-butylsulfonyl, tert-butylsulfonyl and pentylsulfonyl.

Examples of the "lower alkylsulfinyl group" include methylsulfinyl, ethylsulfinyl, propylsulfinyl, isopropylsulfinyl and butylsulfinyl.

Examples of the "lower alkylthio group" include methylthio, ethylthio, propylthio, isopropylthio, butylthio, isobutylthio and sec-butylthio.

Specific examples of the group shown by formula:

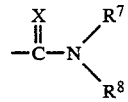

wherein each of $R^7$ and $R^8$ independently represents a hydrogen atom or a lower alkyl group which may be substituted with 1 or 2 substituents, which may be the same or different and are selected from the group consisting of a hydroxy group and a lower alkoxy group, or both $R^7$ and $R^8$ are combined together with the nitrogen atom adjacent thereto to form a saturated nitrogen-containing heterocyclic group; and X represents an oxygen atom or a sulfur atom, include: carbamoyl, N-methylcarbamoyl, N-ethylcarbamoyl, N-(2-hydroxyethyl)carbamoyl, N-(2-methoxyethyl)carbamoyl, N-(2-hydroxypropyl)carbamoyl, N-(2-methoxypropyl)carbamoyl, N-N-dimethylcarbamoyl, N-ethyl-N-methylcarbamoyl, N-(2-hydroxyethyl)-N-methylcarbamoyl, N-(2-methoxyethyl)-N-methylcarbamoyl, N,N-diethylcarbamoyl, N,N-dipropylcarbamoyl, N-ethyl-N-(2-hydroxyethyl)-carbamoyl, N-ethyl-N-(2-methoxyethyl)carbamoyl, N,N-di(2-hydroxyethyl)carbamoyl, N,N-di(2-methoxyethyl)carbamoyl, pyrrolidinocarbonyl, piperidinocarbonyl, morpholinocarbonyl, thiocarbamoyl, N-methylthiocarbamoyl, N-ethylthiocarbamoyl, N-(2-hydroxyethyl)thiocarbamoyl, N-(2-methoxyethyl)thiocarbamoyl, N-(2-methoxypropyl)thiocarbamoyl, N,N-dimethylthiocarbamoyl, N-ethyl-N-methylthiocarbamoyl, N-(2-hydroxyethyl)-N-methylthiocarbamoyl, N-(2-methoxyethyl)-N-methylthiocarbamoyl, N,N-diethylthiocarbamoyl and pyrrolidinothiocarbonyl.

Specific examples of the group shown by formula:

wherein each $R^{11}$ and $R^{12}$ independently represents a hydrogen atom, a lower alkyl group or a lower alkanoyl group, or both are combined together to form a 5- to 7-membered nitrogen-containing saturated heterocyclic ring having 3 to 6 carbon atoms together with the nitrogen atom adjacent thereto, wherein one methylene group not adjacent to the nitrogen atom for forming the ring may be replaced by an oxy group or a thio group and one methylene group adjacent to the nitrogen atom may be replaced by a carbonyl group, include: amino, N-methylamino, N,N-dimethylamino, N-ethyl-N-methylamino, N,N-diethylamino, N-acetylamino, N-acetyl-N-methylamino, N-propionylamino, N-methyl-N-propionylamino, 1,3-thiazolidin-3-yl, pyrrolidino, piperidino, morpholino, Perhydro-1,4-thiazin-4-yl, perhydroazepin-1-yl, 2-pyrrolidon-1-yl and 2-piperidon-1-yl.

Examples of the "divalent alkylene chain having 1 to 5 carbon atoms which may be substituted with a lower alkyl group (one optional methylene group in which alkylene chain may be replaced by one group selected from the group consisting of an oxy group, a thio group, a sulfinyl group, a sulfonyl group or a group shown by formula: —$NR^6$— wherein $R^6$ represents a hydrogen atom or a lower alkyl group); provided that the said methylene group is not the methylene group adjacent to the oxygen atom at the 8-position of the isoquinoline ring" include: —$CH_2$—, —$CH(CH_3)$—, —$CH(CH_2$—$CH_3)$—, —$(CH_2)_2$—, —$CH(CH_3)$—$CH_2$—, —$CH_2$—$CH(CH_3)$—, —O—$CH_2$—, —S—$CH_2$—, —$N(CH_3)$—$CH_2$—, —$(CH_2)_3$—, —$CH(CH_3)$—$(CH_2)_2$—, —$CH_2$—$CH(CH_3)$—$CH_2$—, —$(CH_2)_2$—$CH(CH_3)$—, —O—$(CH_2)_2$—, —S—$(CH_2)_2$—, —SO—$(CH_2)_2$—, —$SO_2$—$(CH_2)_2$—, —NH—$(CH_2)_2$—, —$NCH_3$—$(CH_2)_2$—, —O—$CH(CH_3)$—$CH_2$—, —S—$CH(CH_3)$—$CH_2$—, —SO—$CH(CH_3)$—$CH_2$—, —$SO_2$—$CH(CH_3)$—$CH_2$—, —NH—$CH(CH_3)$—$CH_2$—, —$N(CH_3)$—$CH(CH_3)$—$CH_2$—, —$(CH_2)_4$—, —$CH(CH_3)$—$(CH_2)_3$—, —$CH_2$—$CH(CH_3)$—$(CH_2)_2$—, —$(CH_2)_2$—$CH(CH_3)$—$CH_2$—, —$(CH_2)_3$—$CH(CH_3)$—, —O—$(CH_2)_3$—, —S—$(CH_2)_3$—, —SO—$(CH_2)_3$—, —$SO_2$—$(CH_2)_3$—, —NH—$(CH_2)_3$—, —$NCH_3$—$(CH_2)_3$—, —$CH_2$—O—$(CH_2)_2$—, —$CH_2$—S—$(CH_2)_2$—, —$CH_2$—SO—$(CH_2)_2$—, —$CH_2$—$SO_2$—$(CH_2)_2$—, —$CH_2$—NH—$(CH_2)_2$—, —$CH_2$—$N(CH_3)$—$(CH_2)_2$—, —$(CH_2)_2$—O—$CH_2$—, —$(CH_2)_2$—S—$CH_2$—, —$(CH_2)_2$—$N(CH_3)$—$CH_2$—, —O—$CH(CH_3)$—$(CH_2)_2$—, —S—$CH(CH_3)$—$(CH_2)_2$—, —$N(CH_3)$—$CH(CH_3)$—$(CH_2)_2$—, —$(CH_2)_5$—, —$CH(CH_3)$—$(CH_2)_4$—, —$(CH_2)_4$—$CH(CH_3)$—, —O—$(CH_2)_4$—, —S—$(CH_2)_4$—, —SO—$(CH_2)_4$—, —$SO_2$—$(CH_2)_4$—, —NH—$(CH_2)_4$—, —$NCH_3$—$(CH_2)_4$—, —$CH_2$—O—$(CH_2)_3$—, —$CH_2$—S—$(CH_2)_3$—, —$CH_2$—SO—$(CH_2)_3$—, —$CH_2$—$SO_2$—$(CH_2)_3$—, —$CH_2$—NH—$(CH_2)_3$—, —$CH_2$—$N(CH_3)$—$(CH_2)_3$—.

Examples of the "divalent alkylene chain having 1 to 4 carbon atoms which may be substituted with a lower alkyl group" include: —$CH_2$—, —$CH(CH_3)$—, —$CH(CH_2$—$CH_3)$—, —$(CH_2)_2$—, —$CH(CH_3)$—$CH_2$—, —$CH_2$—$CH(CH_3)$—, —$(CH_2)_3$—, —$CH(CH_3)$—$(CH_2)_2$—, —$CH_2$—$CH(CH_3)$—$CH_2$—, —$(CH_2)_2$—$CH(CH_3)$—, —$(CH_2)_4$—, —$CH(CH_3)$—$(CH_2)_3$—, —$CH_2$—$CH(CH_3)$—$(CH_2)_2$—, —$(CH_2)_2$—$CH(CH_3)$—$CH_2$—, —$(CH_2)_3$—$CH(CH_3)$—.

Preferred compounds of the present invention are the isoquinoline derivatives of formula (I), wherein each of $R^1$ and $R^2$ independently represents a lower alkyl group or both are combined together to form a methylene group; $R^4$ represents a phenyl group wherein 1 to 3 optional hydrogen atoms on the benzene ring may be replaced by 1 to 3 substituents selected from the group consisting of a lower alkoxy group and a methylenedioxy group, or a pyridyl group; $X^2$ represents $CH^2$ or $CH_2CH_2$; $R^3$ represents a group represented by formula:

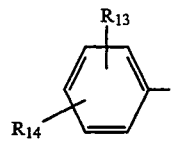

wherein $R^{13}$ represents a hydrogen atom or a lower alkoxy group; and $R^{14}$ represents an amino group, an N-mono-lower alkylamino group or an N,N-di-lower alkylamino group or represents a group shown by formula:

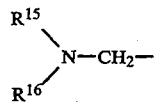

wherein each of $R^{15}$ and $R^{16}$ independently represents a hydrogen atom or a lower alkyl group wherein a hydrogen atom on the carbon atom not adjacent to the nitrogen atom may be replaced by a hydroxy group or a lower alkoxy group; or both $R^{15}$ and $R^{16}$ are combined together with the nitrogen atom adjacent thereto to form a 5- to 7-membered nitrogen-containing saturated heterocyclic ring having 3 to 6 carbon atoms and in this case, one optional methylene group not adjacent to the nitrogen atom may be replaced by one group selected from the group consisting of oxy, thio, sulfinyl, sulfonyl or a group shown by formula: —$NR^{17}$— wherein $R^{17}$ represents a hydrogen atom or a lower alkyl group, or a pyridyl group wherein 1 or 2 hydrogen atoms on the pyridine ring may be replaced by 1 or 2 substituents selected from the group consisting of a lower alkoxy group and an N,N-di-lower alkylaminomethyl group.

Processes for preparing the compounds (I) of the present invention are explained below.

The compounds of the present invention represented by general formula (I) described above can be prepared by alkanoylation, alkoxycarbonylation, carbamoylation or sulfonylation of 1,2,3,4-tetrahydroisoquinolin-8-ol derivatives (II) represented by general formula (II):

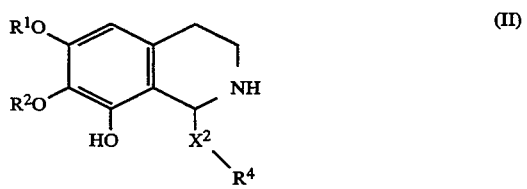

wherein $R^1$, $R^2$, $X^2$ and $R^4$ are as described above; and then condensing the resulting derivatives (III):

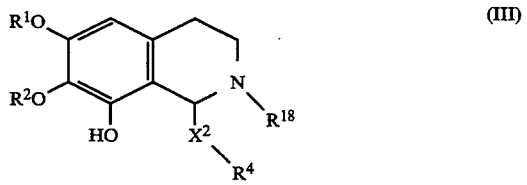

wherein $R^1$, $R^2$, $X^2$ and $R^4$ have the same significations as described above; and $R^{18}$ represents a lower alkoxycarbonyl group, a lower alkylsulfonyl group, a group represented by formula:

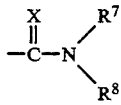

wherein $R^7$ and $R^8$ have the same significances as described above, or a lower alkanoyl group wherein the lower alkanoyl group may be substituted with 1 or 2 substituents selected from the group consisting of a lower alkylsulfinyl group, a lower alkylthio group, a hydroxy group, a lower alkoxy group and an N,N-di-lower alkylamino group, on the hydroxy group at the 8-position of the isoquinoline ring, with compounds (IV) represented by general formula (IV):

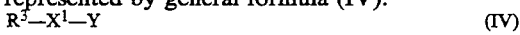
$$R^3\text{—}X^1\text{—}Y \qquad \text{(IV)}$$

wherein $R^3$ and $X^1$ are as described above; and Y represents a leaving group which is generally replacable by an aryloxy group, in the presence of a base (referred to as Process 1).

Alternatively, the compounds of the present invention can be prepared by performing substitution of one halogen atom in $\alpha,\alpha'$-dihaloxylenes (o-, m-, p-) with the compounds (III) in a manner similar to Process 1 and then substituting another halogen atom remained with primary or secondary amines (referred to as Process 2).

Furthermore, compounds obtained in Process 1 or Process 2 in which $R^{18}$ is formyl can be converted into the desired compounds by subjecting the formyl compounds to alkali hydrolysis to remove the formyl, if necessary, then subjecting the resulting derivatives (V):

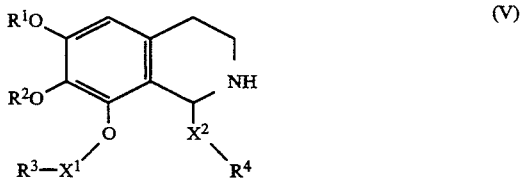

wherein $R^1$, $R^2$, $R^3$, $R^4$, $X^1$ and $X^2$ have the same significances as described above, to alkanoylation, alkoxycarbonylation, carbamoylation or sulfonylation at the 2-position of the isoquinoline ring, and further where a suitable leaving group is present on the introduced substituent of the compounds obtained by the alkanoylation, substituting the leaving group with nucleophilic agents such as thiol compounds, primary or secondary amines and amide compounds (referred to as Process 3). Where the compounds obtained by Process 3 contain an acylthio group, the acylthio group may be converted into a mercapto group, if desired, by alkali hydrolysis (referred to as Process 4). Where the compounds obtained by Processes 1 to 3 contain a nitro group in $R^3$ and/or $R^4$ the nitro group may be converted into a primary amino group using an appropriate reducing agent (referred to as Process 5). Where the compounds obtained by Processes 1 to 3 contain a thio group, the thio group may be converted into a sulfinyl group or a sulfonyl group using an appropriate oxidizing agent, if necessary (Process 6).

Hereafter these processes are described more specifically.

PROCESS 1

The alkanoylation of Compound (II) at the 2-position of the isoquinoline ring can be performed by reacting a carboxylic acid reactive derivative (for example, an acid halide, an acid anhydride, an activated amide, an activated ester) corresponding to the alkanoyl group to be introduced, with (II) in an appropriate solvent (for example, chloroform, dichloromethane, dimethylformamide, tetrahydrofuran, 1,4-dioxane) at 0° C. to room temperature, if necessary, in the presence of an appropriate basic for example, triethylamine, pyridine, 4-N,N-dimethylaminopyridine). The alkoxycarbonylation and sulfonylation may be conducted in a similar manner by reacting (II) with an alkoxycarbonyl halide or a sulfonyl halide corresponding to the group to be introduced. The carbamoylation may be effected either by reacting (II) with a carbamoyl halide corresponding to the group to be introduced, in the same manner as in the alkanoylation, or by reacting isocyanate or isothiocyanate with (II) at 0° C. to room temperature in an appropriate solvent (for example, chloroform, dichloromethane, tetrahydrofuran, 1,4-dioxane).

The condensation of Compound (III) with Compound (IV) is carried out preferably in an appropriate solvent. Examples of the solvent used are acetone, acetonitrile, methanol, 1,4-dioxane, tetrahydrofuran, dimethylsulfoxide and dimethylformamide. Examples of the base used in the reaction include inorganic bases such as alkali metal carbonates, alkali metal hydrogencarbonate, alkali metal hydroxides, alkali metal hydrides and alkali metal alkoxides. In general, the reaction can be carried out by dissolving Compound (III) in the solvent described above, adding a suitable base to the solution, further adding Compound (IV) and then reacting the mixture at 0° C. to 80° C.

PROCESS 2

The condensation of Compound (III) with $\alpha,\alpha'$-dihaloxylenes (o-, m-, p-) is carried out in the same manner as in Process 1. The substitution of one halogen atom remained on the group introduced in the resulting compound may be performed by adding an excess amount of a primary or secondary amine to be introduced in an appropriate solvent (for example, methanol, ethanol, 1,4-dioxane, dimethylformamide or dimethylsulfoxide) and reacting them at 0° C. to the boiling point of the solvent.

PROCESS 3

The synthesis of Compound (V) via deformylation by alkali hydrolysis can be performed by adding 1 equivalent to an excess amount of alkali metal hydroxide aqueous solution to the starting compound in an appropriate solvent (methanol, ethanol or 1,4-dioxane) and reacting them at room temperature to the boiling point of the solvent. The alkanoylation, alkoxycarbonylation, carbamoylation and sulfonylation may be performed in a manner similar to Process 1. Where the alkanoyl group has a splitting off group, the introduction of the thiol compound by substitution of this splitting off group can be performed by reacting the thiol compound with the starting compound in a suitable solvent (for example, methanol, ethanol, chloroform, tetrahydrofuran, dimethylformamide or dimethyl sulfoxide) at 0° C. to the boiling point of the solvent, if necessary, in the presence of an appropriate base (for example, an organic base such as triethylamine and pyridine; an inorganic base such as an alkali metal hydroxide, an alkali metal carbonate, an alkali metal hydrogencarbonate, an alkali metal hydride and an alkali metal alkoxide).

The introduction of the primary or secondary amine can be performed as in Process 2. The introduction of the amide compound may be carried out by reacting the amide compound with the starting compound in an appropriate solvent (tetrahydrofuran, dimethylformamide or 1,4-dioxane) at 0° C. to the boiling point of the solvent in the presence of an appropriate base (for example, an alkali metal hydride).

PROCESS 4

The conversion of the acylthio group into the mercapto group by alkali hydrolysis may be conducted by adding an aqueous solution of an appropriate base (for example, an alkali metal hydroxide, an alkali metal carbonate, an alkali metal hydrogencarbonate, ammonia) in an appropriate solvent (for example, methanol, ethanol, 1,4-dioxane) to the starting compound and then reacting them at 0° C. to the boiling point of the solvent.

PROCESS 5

The conversion of the nitro group to the primary amino group through reduction may be carried out by adding tin (II) chloride to the starting compound in an appropriate solvent (for example, ethanol or ethyl acetate) and reacting them at 60° C. to the boiling point of the solvent.

PROCESS 6

The conversion of the thio group into the sulfinyl group or sulfonyl group by oxidation may be carried out by adding an appropriate oxidizing agent (for example, oxone, m-chloroperbenzoic acid, hydrogen peroxide) to the starting compound in an appropriate solvent (for example, chloroform, dichloromethane, acetic acid or acetone) and reacting them at 0° C. to 60° C. An amount of the oxidizing agent used is in the range of 1 to 1.2 equivalents in the case of sulfinylation and in the range of 2 to 3 equivalents in the case of sulfonylation, based on the starting compound having the thio group.

Compounds (I) obtained by these processes contain stereoisomers based on the presence of asymmetric carbon at the 1-position of the isoquinoline ring. Where the starting Compound (II) is a racemic mixture, the racemic mixture is subjected to optical resolution using an appropriate optically active acid in a conventional manner and the respective processes described above are applied to the products, whereby the respective stereoisomers may be synthesized. As the appropriate acid used for the optical resolution, there are (+)-tartaric acid, (−)-tartaric acid, (+)-dibenzoyltartaric acid and (−)-dibenzoyltartaric acid. The starting material, 1,2,3,4-tetrahydroisoquinoline derivatives [II] may be synthesized by the known method (see PCT/JP89/00825, WO90/02119). That is, Compound [II] may be prepared from phenethylamines via Bischler-Napieralski reaction.

The starting Compound (IV) may be synthesized by converting the hydroxy group of aminoalcohols obtained by known methods [for example, see Japanese Patent Application KOKAI (Laid-Open) No. 55-53247, J. Med. Chem., 27, 1047 (1984)] into a splitting off group in a conventional manner. That is, Compound (IV) may be synthesized either by reacting with a reagent such as thionyl chloride, thionyl bromide, phosphorus pentachloride, phosphorus oxychloride, etc. in the absence of any solvent or in an appropriate solvent (for example, chloroform or dichloromethane) thereby to convert into the halide or by reacting with a reagent such as methanesulfonyl chloride and p-toluenesulfonyl chloride to convert into the mesylate or rosylate.

Preferred compounds of the present invention are listed in the following Table.

| Compound No. | $R^1$ | $R^2$ | $R^3$ | $R^4$ | $R^5$ | $X^1$ | $X^2$ |
|---|---|---|---|---|---|---|---|
| 1 | $CH_3-$ | $CH_3-$ | 3-((CH_3)_2NCH_2)-C_6H_4- | 4-OCH_3-C_6H_4- | $-CHO$ | $-CH_2-$ | $-CH_2-$ |
| 2 | $CH_3-$ | $CH_3-$ | 3-(pyrrolidin-1-ylmethyl)-C_6H_4- | 4-OCH_3-C_6H_4- | $-CHO$ | $-CH_2-$ | $-CH_2-$ |
| 3 | $CH_3-$ | $CH_3-$ | 3-(morpholin-4-ylmethyl)-C_6H_4- | 4-OCH_3-C_6H_4- | $-CHO$ | $-CH_2-$ | $-CH_2-$ |
| 4 | $CH_3-$ | $CH_3-$ | 4-((CH_3)_2NCH_2)-C_6H_4- | 4-OCH_3-C_6H_4- | $-CHO$ | $-CH_2-$ | $-CH_2-$ |
| 5 | $CH_3-$ | $CH_3-$ | 3-((4-methylpiperazin-1-yl)methyl)-C_6H_4- | 4-OCH_3-C_6H_4- | $-CHO$ | $-CH_2-$ | $-CH_2-$ |

-continued

(I)

| Compound No. | $R^1$ | $R^2$ | $R^3$ | $R^4$ | $R^5$ | $X^1$ | $X^2$ |
|---|---|---|---|---|---|---|---|
| 6 | $CH_3-$ | $CH_3-$ | Ph— | ![4-methoxyphenyl] | —CHO | $-CH_2NCH_2CH_2CH_2-$ $\quad\quad\;\;\;\; CH_3$ | $-CH_2-$ |
| 7 | $CH_3-$ | $CH_3-$ | 3-((CH$_3$)$_2$NCH$_2$)-phenyl | ![4-methoxyphenyl] | —CHO | $-CH_2-$ | $-CH_2-$ |
| 8 | $CH_3-$ | $CH_3-$ | 4-((CH$_3$)$_2$NCH$_2$)-phenyl | ![3-methoxyphenyl] | —CHO | $-CH_2-$ | $-CH_2-$ |
| 9 | $CH_3-$ | $CH_3-$ | 3-methyl-4-methoxy-((CH$_3$)$_2$NCH$_2$)-phenyl | ![3-methoxyphenyl] | —CHO | $-CH_2-$ | $-CH_2-$ |
| 10 | $CH_3-$ | $CH_3-$ | 3-(morpholinomethyl)phenyl | ![3-methoxyphenyl] | —CHO | $-CH_2-$ | $-CH_2-$ |

-continued (I)

| Compound No. | R¹ | R² | R³ | R⁴ | R⁵ | X¹ | X² |
|---|---|---|---|---|---|---|---|
| 11 | CH₃— | CH₃— | 2-pyridyl | 3-methoxyphenyl | —CHO | —CH₂— | —CH₂— |
| 12 | CH₃— | CH₃— | 3-pyridyl | 3-methoxyphenyl | —CHO | —CH₂— | —CH₂— |
| 13 | CH₃— | CH₃— | 3-((CH₃)₂NCH₂)phenyl | 2-methoxyphenyl | —CHO | —CH₂— | —CH₂— |
| 14 | CH₃— | CH₃— | 3-((CH₃)₂NCH₂)phenyl | 3,4-dimethoxyphenyl | —CHO | —CH₂— | —CH₂— |
| 15 | CH₃— | CH₃— | 3-((CH₃)₂NCH₂)phenyl | 4-methoxy-2-methyl-5-methoxyphenyl | —CHO | —CH₂— | —CH₂— |

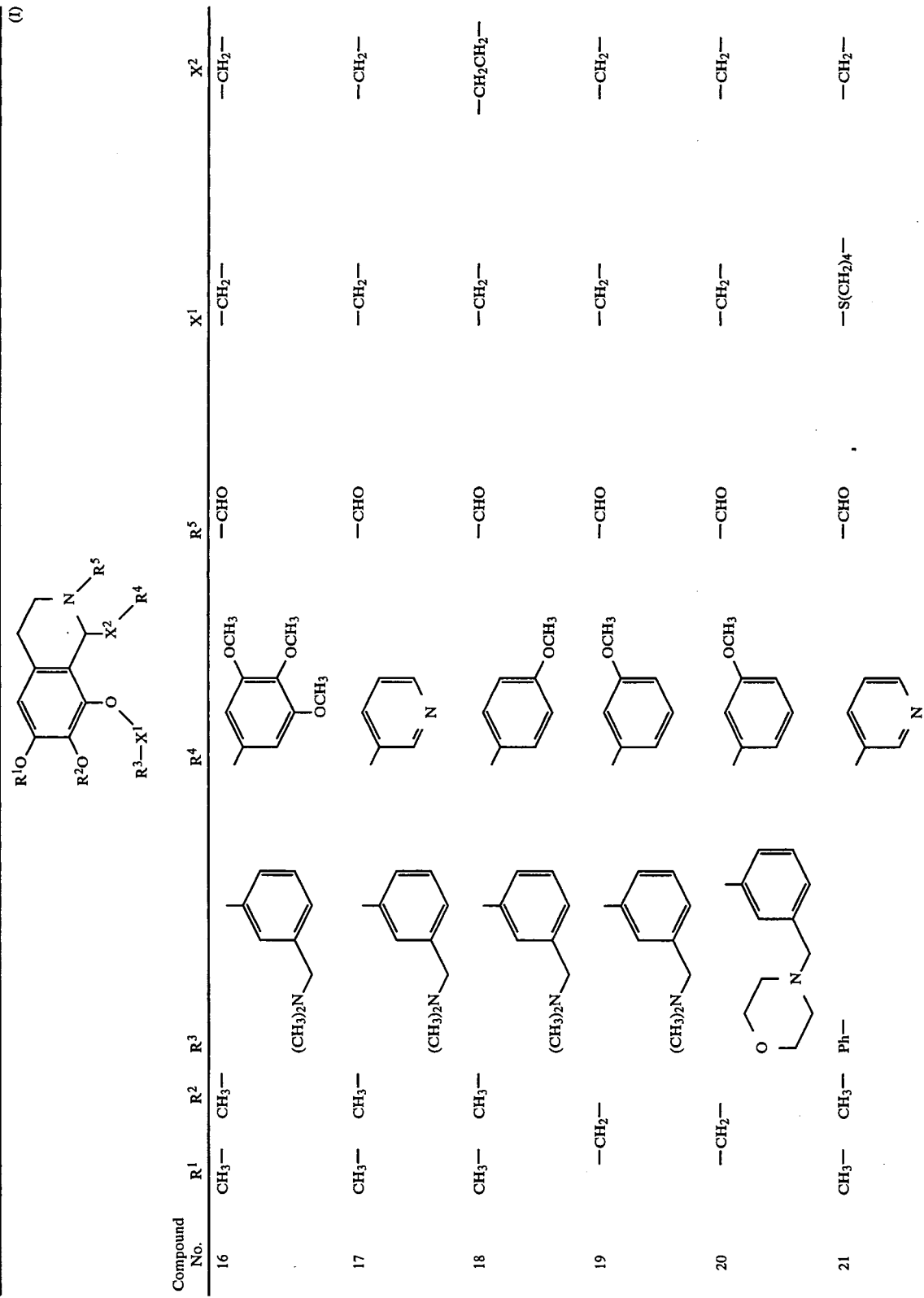

-continued

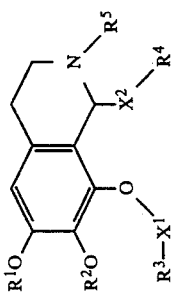
(I)

| Compound No. | R¹ | R² | R³ | R⁴ | R⁵ | X¹ | X² |
|---|---|---|---|---|---|---|---|
| 22 | $CH_3-$ | $CH_3-$ | 3-($CH_3NH$-$CH_2$-)phenyl | 3-$OCH_3$-phenyl | $-CHO$ | $-CH_2-$ | $-CH_2-$ |
| 23 | $CH_3-$ | $CH_3-$ | 3-(4-methylpiperazin-1-ylmethyl)phenyl | 3-$OCH_3$-phenyl | $-CHO$ | $-CH_2-$ | $-CH_2-$ |
| 24 | $CH_3-$ | $CH_3-$ | 3-(thiomorpholin-4-ylmethyl)phenyl | 3-$OCH_3$-phenyl | $-CHO$ | $-CH_2-$ | $-CH_2-$ |
| 25 | $CH_3-$ | $CH_3-$ | 3-(thiazolidin-3-ylmethyl)phenyl | 3-$OCH_3$-phenyl | $-CHO$ | $-CH_2-$ | $-CH_2-$ |
| 26 | $CH_3-$ | $CH_3-$ | 2-(($CH_3)_2N$-$CH_2$-)phenyl | 3-$OCH_3$-phenyl | $-CHO$ | $-CH_2-$ | $-CH_2-$ |

-continued

(I)

| Compound No. | R¹ | R² | R³ | R⁴ | R⁵ | X¹ | X² |
|---|---|---|---|---|---|---|---|
| 27 | $CH_3-$ | $CH_3-$ | 2-($(CH_3)_2NCH_2$)-phenyl | 4-$OCH_3$-phenyl | $-CHO$ | $-CH_2-$ | $-CH_2-$ |
| 28 | $CH_3-$ | $CH_3-$ | 3-($CH_3$N($CH_2CH_2OH$)$CH_2$)-phenyl | 4-$OCH_3$-phenyl | $-CHO$ | $-CH_2-$ | $-CH_2-$ |
| 29 | $CH_3-$ | $CH_3-$ | 2-($(CH_3)_2NCH_2$)-phenyl | 3,5-di-$OCH_3$-phenyl | $-CHO$ | $-CH_2-$ | $-CH_2-$ |
| 30 | $CH_3-$ | $CH_3-$ | 3-($(CH_3)_2NCH_2$)-phenyl | 4-$OCH_3$-phenyl | $-COCH_2OH$ | $-CH_2-$ | $-CH_2-$ |
| 31 | $CH_3-$ | $CH_3-$ | 3-($(CH_3)_2NCH_2$)-phenyl | 4-$OCH_3$-phenyl | $-CO(CH_2)_2OH$ | $-CH_2-$ | $-CH_2-$ |
| 32 | $CH_3-$ | $CH_3-$ | 3-($(CH_3)_2NCH_2$)-phenyl | 4-$OCH_3$-phenyl | $-COCH(OH)CH_3$ | $-CH_2-$ | $-CH_2-$ |

-continued (I)

| Compound No. | $R^1$ | $R^2$ | $R^3$ | $R^4$ | $R^5$ | $X^1$ | $X^2$ |
|---|---|---|---|---|---|---|---|
| 33 | CH₃— | CH₃— | (CH₃)₂N(CH₂)— (meta-benzyl) | 4-OCH₃-phenyl | —COCH₂OCH₃ | —CH₂— | —CH₂— |
| 34 | CH₃— | CH₃— | (CH₃)₂N(CH₂)— (meta-benzyl) | 3-OCH₃-phenyl | —COCH₂OH | —CH₂— | —CH₂— |
| 35 | CH₃— | CH₃— | (CH₃)₂N(CH₂)— (meta-benzyl) | 3-OCH₃-phenyl | —CO(CH₂)₂OH | —CH₂— | —CH₂— |
| 36 | CH₃— | CH₃— | (CH₃)₂N(CH₂)— (meta-benzyl) | 3-OCH₃-phenyl | —COCH₂OCH₃ | —CH₂— | —CH₂— |
| 37 | CH₃— | CH₃— | (CH₃)₂N(CH₂)— (meta-benzyl) | 3-OCH₃-phenyl | —COCH₂N(CH₃)COCH₃ | —CH₂— | —CH₂— |

-continued (I)

| Compound No. | $R^1$ | $R^2$ | $R^3$ | $R^4$ | $R^5$ | $X^1$ | $X^2$ |
|---|---|---|---|---|---|---|---|
| 38 | $CH_3-$ | $CH_3-$ | $(CH_3)_2N\text{-}\underset{}{\underset{}{\bigcirc}}\text{-}CH_2\text{-}$ | $\underset{}{\underset{}{\bigcirc}}\text{-}OCH_3$ | $-SO_2CH_3$ | $-CH_2-$ | $-CH_2-$ |
| 39 | $CH_3-$ | $CH_3-$ | $(CH_3)_2N\text{-}\underset{}{\underset{}{\bigcirc}}\text{-}CH_2\text{-}$ | $\underset{}{\underset{}{\bigcirc}}\text{-}OCH_3$ | $-COCH_3$ | $-CH_2-$ | $-CH_2-$ |
| 40 | $CH_3-$ | $CH_3-$ | $(CH_3)_2N\text{-}\underset{}{\underset{}{\bigcirc}}\text{-}CH_2\text{-}$ | $\underset{}{\underset{}{\bigcirc}}\text{-}OCH_3$ | $-CONHCH_3$ | $-CH_2-$ | $-CH_2-$ |
| 41 | $CH_3-$ | $CH_3-$ | $(CH_3)_2N\text{-}\underset{}{\underset{}{\bigcirc}}\text{-}CH_2\text{-}$ | $\underset{}{\underset{}{\bigcirc}}\text{-}OCH_3$ | $-CSNHCH_3$ | $-CH_2-$ | $-CH_2-$ |
| 42 | $CH_3-$ | $CH_3-$ | $(CH_3)_2N\text{-}\underset{}{\underset{}{\bigcirc}}\text{-}CH_2\text{-}$ | $\underset{}{\underset{}{\bigcirc}}\text{-}OCH_3$ | $-CONH(CH_2)_2OH$ | $-CH_2-$ | $-CH_2-$ |
| 43 | $CH_3-$ | $CH_3-$ | $(CH_3)_2N\text{-}\underset{}{\underset{}{\bigcirc}}\text{-}CH_2\text{-}$ | $\underset{}{\underset{}{\bigcirc}}\text{-}OCH_3$ | $-CON(CH_3)_2$ | $-CH_2-$ | $-CH_2-$ |

-continued (I)

| Compound No. | $R^1$ | $R^2$ | $R^3$ | $R^4$ | $R^5$ | $X^1$ | $X^2$ |
|---|---|---|---|---|---|---|---|
| 44 | $CH_3$— | $CH_3$— | 3-$(CH_3)_2NCH_2$-phenyl | 4-$CH_3O$-phenyl | —$CONH_2$ | —$CH_2$— | —$CH_2$— |
| 45 | $CH_3$— | $CH_3$— | 2-$(CH_3)_2NCH_2$-phenyl | 4-$CH_3O$-phenyl | —$CONHCH_3$ | —$CH_2$— | —$CH_2$— |
| 46 | $CH_3$— | $CH_3$— | 3-$(CH_3)_2NCH_2$-phenyl | 4-$CH_3O$-phenyl | —$COCH_2OH$ | —$CH_2$— | —$CH_2$— |
| 47 | $CH_3$— | $CH_3$— | 3-$(CH_3)_2NCH_2$-phenyl | 4-$CH_3O$-phenyl | —$COCH_2SCOCH_3$ | —$CH_2$— | —$CH_2$— |
| 48 | $CH_3$— | $CH_3$— | 3-$(CH_3)_2NCH_2$-phenyl | 4-$CH_3O$-phenyl | —$COCH_2SCH_3$ | —$CH_2$— | —$CH_2$— |

-continued (I)

| Compound No. | $R^1$ | $R^2$ | $R^3$ | $R^4$ | $R^5$ | $X^1$ | $X^2$ |
|---|---|---|---|---|---|---|---|
| 49 | $CH_3-$ | $CH_3-$ | | 4-$OCH_3$-phenyl | N-morpholinyl-$CH_2COCH_3$ | $-CH_2-$ | $-CH_2-$ |
| 50 | $CH_3-$ | $CH_3-$ | $(CH_3)_2N$-3-benzyl | 4-$OCH_3$-phenyl | $-COCH_2SCOCH_3$ | $-CH_2-$ | $-CH_2-$ |
| 51 | $CH_3-$ | $CH_3-$ | $(CH_3)_2N$-3-benzyl | 3-$OCH_3$-phenyl | $-COCH_2SCOCH_3$ | $-CH_2-$ | $-CH_2-$ |
| 52 | $CH_3-$ | $CH_3-$ | $(CH_3)_2N$-2-benzyl | 2,4-di-$OCH_3$-phenyl | $-COCH_2SCOCH_3$ | $-CH_2-$ | $-CH_2-$ |
| 53 | | $-CH_2-$ | morpholinyl-3-benzyl | 3-$OCH_3$-phenyl | $-COCH_2SCOCH_3$ | $-CH_2-$ | $-CH_2-$ |
| 54 | $CH_3-$ | $CH_3-$ | $(CH_3)_2N$-2-benzyl | 3-$OCH_3$-phenyl | N-(2-oxopyrrolidinyl)-$CH_2COCH_3$ | $-CH_2-$ | $-CH_2-$ |

-continued (I)

| Compound No. | $R^1$ | $R^2$ | $R^3$ | $R^4$ | $R^5$ | $X^1$ | $X^2$ |
|---|---|---|---|---|---|---|---|
| 55 | $CH_3-$ | $CH_3-$ | $(CH_3)_2N\text{-}m\text{-}C_6H_4CH_2-$ | $p\text{-}CH_3OC_6H_4-$ | $-CO_2CH_3$ | $-CH_2-$ | $-CH_2-$ |
| 56 | $CH_3-$ | $CH_3-$ | $(CH_3)_2N\text{-}m\text{-}C_6H_4CH_2-$ | $p\text{-}CH_3OC_6H_4-$ | $-SO_2CH_3$ | $-CH_2-$ | $-CH_2-$ |
| 57 | $CH_3-$ | $CH_3-$ | $(CH_3)_2N\text{-}m\text{-}C_6H_4CH_2-$ | $p\text{-}CH_3OC_6H_4-$ | $-COCH_3$ | $-CH_2-$ | $-CH_2-$ |
| 58 | $CH_3-$ | $CH_3-$ | $(CH_3)_2N\text{-}m\text{-}C_6H_4CH_2-$ | $p\text{-}CH_3OC_6H_4-$ | $-COCH_2N(CH_3)_2$ | $-CH_2-$ | $-CH_2-$ |
| 59 | $CH_3-$ | $CH_3-$ | $(CH_3)_2N\text{-}m\text{-}C_6H_4CH_2-$ | $m\text{-}CH_3OC_6H_4-$ | $-CO_2CH_3$ | $-CH_2-$ | $-CH_2-$ |

-continued (I)

| Compound No. | R¹ | R² | R³ | R⁴ | R⁵ | X¹ | X² |
|---|---|---|---|---|---|---|---|
| 60 | CH₃— | CH₃— | CH₃-N(piperazinyl)-CH₂-(3-methylphenyl) | 3-OCH₃-phenyl | —CO₂CH₃ | —CH₂— | —CH₂— |
| 61 | CH₃— | CH₃— | 2-pyridyl | 3-OCH₃-phenyl | —CONHCH₃ | —CH₂— | —CH₂— |
| 62 | CH₃— | CH₃— | 3-pyridyl | 3-OCH₃-phenyl | —CONHCH₃ | —CH₂— | —CH₂— |
| 63 | CH₃— | CH₃— | 4-pyridyl | 3-OCH₃-phenyl | —CONHCH₃ | —CH₂— | —CH₂— |
| 64 | CH₃— | CH₃— | (3-methylphenyl)-CH₂-NH-CH₃ | 3-OCH₃-phenyl | —CONHCH₃ | —CH₂— | —CH₂— |
| 65 | CH₃— | CH₃— | HN(piperazinyl)-CH₂-(3-methylphenyl) | 3-OCH₃-phenyl | —CONHCH₃ | —CH₂— | —CH₂— |

-continued $$(I)$$

| Compound No. | R¹ | R² | R³ | R⁴ | R⁵ | X¹ | X² |
|---|---|---|---|---|---|---|---|
| 66 | CH₃— | CH₃— | 3-(4-methylpiperazin-1-ylmethyl)phenyl | 3-methyl-4-methoxyphenyl | —CONHCH₃ | —CH₂— | —CH₂— |
| 67 | CH₃— | CH₃— | 3-(morpholin-4-ylmethyl)phenyl | 3-methyl-4-methoxyphenyl | —CONHCH₃ | —CH₂— | —CH₂— |
| 68 | CH₃— | CH₃— | 3-((CH₃)₂NCH₂)phenyl | 3-methyl-4-methoxyphenyl | —COCH₂OCOCH₃ | —CH₂— | —CH₂— |
| 69 | CH₃— | CH₃— | 3-((CH₃)₂NCH₂)phenyl | 3-methyl-4-methoxyphenyl | —COCH₂OCOCH₂OH | —CH₂— | —CH₂— |
| 70 | CH₃— | CH₃— | 3-((CH₃)₂NCH₂)phenyl | 3-methyl-4-methoxyphenyl | —COCH₂SH | —CH₂— | —CH₂— |

-continued
(I)
| Compound No. | R¹ | R² | R³ | R⁴ | R⁵ | X¹ | X² |
|---|---|---|---|---|---|---|---|
| 71 | $CH_3-$ | $CH_3-$ | 3-$O_2N$-phenyl | 4-$OCH_3$-phenyl | $-CHO$ | $-CH_2-$ | $-CH_2-$ |
| 72 | $CH_3-$ | $CH_3-$ | 3-$H_2N$-phenyl | 4-$OCH_3$-phenyl | $-CHO$ | $-CH_2-$ | $-CH_2-$ |
| 73 | $CH_3-$ | $CH_3-$ | 3-(morpholinyl-S(O)-)phenyl | 4-$OCH_3$-phenyl | $-CHO$ | $-CH_2-$ | $-CH_2-$ |
| 75 | $CH_3-$ | $CH_3-$ | 4-$(CH_3)_2N$-phenyl | 4-$OCH_3$-phenyl | $-COCH_2OH$ | $-CH_2-$ | $-CH_2-$ |

The pharmacological activities of the compounds according to the present invention are described below.

Effect on ventricular fibrillation and mortality induced by coronary artery occlusion and reperfusia in rats:

Under anesthesia with pentobarbital, male Spraque Dawley (SD) rats were thoracotomized. The compounds of the present invention were studied with respect to the influence on ventricular fibrillation and mortality induced by reperfusion after ligation of the left coronary artery for 5 minutes. At the same time, blood pressure and heart rate were determined through a catheter inserted into the carotid artery. Each test compound was intravenously administered 2 minutes prior to the ligation. The results are shown in Table 1. The hydrochloride of Compound 1 was intraduodenally administered 30 minutes before the ligation. The results are shown in Table 2.

TABLE 1

Effect on ventricular fibrillation and mortality induced by reperfusion after coronary artery ligation in rats (intravenous administration)

| Test Compound | Dose (mg/kg) | Number of animals | Incident rate of ventricular fibrillation (%) | Mortality rate (%) | Change in blood pressure (%) | Change in heart rate (%) |
|---|---|---|---|---|---|---|
| Control |   | 5 | 100 | 100 | 6.3 | −6.8 |
| Cpd. 1 | 1 | 5 | 20 | 0 | 1.8 | −15.0 |
| Cpd. 15 | 1 | 5 | 20 | 0 | 1.9 | −9.9 |
| Cpd. 17 | 1 | 5 | 0 | 0 | 10.0 | −12.5 |
| Cpd. 18 | 1 | 5 | 60 | 20 | 3.7 | −13.3 |
| Cpd. 33 | 1 | 5 | 40 | 20 | 7.2 | −11.4 |
| Cpd. 40 | 1 | 5 | 40 | 0 | −0.5 | −11.5 |
| Cpd. 43 | 1 | 5 | 20 | 0 | 6.8 | −11.6 |
| Cpd. 46 | 1 | 5 | 20 | 20 | −5.2 | −21.3 |
| Cpd. 49 | 1 | 5 | 0 | 0 | 1.0 | −9.3 |
| Cpd. 50 | 1 | 5 | 60 | 40 | 5.2 | −13.8 |
| Cpd. 52 | 1 | 5 | 20 | 0 | −8.8 | −15.6 |
| Cpd. 55 | 1 | 5 | 40 | 20 | 6.4 | −11.5 |
| Cpd. 58 | 1 | 5 | 0 | 0 | −4.0 | −7.9 |
| Cpd. 59 | 1 | 5 | 0 | 0 | 1.3 | −16.5 |
| Cpd. 67 | 1 | 5 | 40 | 40 | 2.6 | −11.7 |
| Cpd. 70 | 1 | 5 | 20 | 20 | −8.5 | −18.1 |
| Lidocaine | 1 | 5 | 100 | 100 | −4.7 | −12.3 |

As shown in Table 1, the compounds of the present invention prevent the occurrence of ventricular fibrillation and mortality rate in the dose of 1.0 mg/kg and the effects were more potent than those with Lidocaine. In this case, a remarkable bradycardiac activity was noted. As demonstrated above, the compounds of the present invention are effective for the conditions induced by reperfusion after coronary artery ligation.

TABLE 2

Effect on ventricular fibrillation and mortality induced by reperfusion after coronary artery ligation in rats (intraduodenal administration)

| Test Compound | Dose (mg/kg) | Number of animals | Incident rate of ventricular fibrillation (%) | Mortality rate (%) |
|---|---|---|---|---|
| Control |   | 6 | 100 | 50 |
| Cpd. 1 hydrochloride | 10 | 6 | 33.3 | 0 |
|  | 50 | 6 | 0 | 0 |

As shown in Table 2, Compound 1 hydrochloride at doses of 10 and 50 mg/kg dose-dependently prevented ventricular fibrillation and mortality rate induced by coronary artery occlusion and reperfusion after intraduodenal administration in rats. This result indicates that intraduodenal administration of the compound of the present invention is effective for the conditions induced by reperfusion after coronary artery ligation.

Effect on ventricular fibrillation induced in dog by reperfusion after coronary artery ligation in dogs:

Under anesthesia with pentobarbital, both sexs beagle dogs were thoracotomized. The compounds of the present invention were studied with respect to the influence on ventricular fibrillation and mortality induced by reperfusion after ligation of the left coronary artery for 30 minutes. Test compound (Compound 1 hydrochloride) and Verapamil were intravenously administered 5 minutes prior to the ligation. The results are shown in Table 3.

TABLE 3

Effect on ventricular fibrillation in dog induced by reperfusion after coronary artery ligation in dogs

| Test Compound | Dose (mg/kg) | Number of animals | Incident rate of ventricular fibrillation (%) |
|---|---|---|---|
| Control |   | 10 | 90 |
| Cpd. 1 Hydrochloride | 1.0 | 10 | 30 |
| Verapamil | 0.1 | 10 | 50 |

As shown in Table 1, Compound 1 hydrochloride markedly inhibited ventricular fibrillation in the dose of 1.0 mg/kg. The effect was more potent than that of Verapamil at the dose of 0.1 mg/kg. As demonstrated above, the compound of the present invention is also effective for the conditions induced in dog by reperfusion after coronary artery ligation in dogs.

The foregoing results of the pharmacological studies reveal that the compounds of the present invention exhibit the anti-arrhythmic activity and bradycardiac activity. Therefore, the present invention can provide an effective method for the treatment of arrhythmia, myocardiac infarction and angina pectoris.

As mode for application of the anti-arrhythmic and bradycardiac agents according to the present invention, various forms can be selected depending upon purposes. There are, for example, oral preparations such as tablets, capsules, powders, granules, liquid or elixir, etc.

and parenteral preparations such as sterilized liquid forms, e.g., liquid or suspension, etc.

Solid preparations may be prepared in the form of tablets, capsules, granules or powders as they are but appropriate additives may also be used for the preparations. Examples of such additives include sugars such as lactose, glucose, etc.; starch of corn, wheat, rice, etc.; fatty acids such as stearic acid, etc.; inorganic salts such as magnesium metasilicate aluminate, anhydrous calcium phosphate, etc.; synthetic high molecular substances such as polyvinylpyrrolidone, polyalkylene glycol, etc.; fatty acid salts such as calcium stearic acid, magnesium stearate, etc.; alcohols such as stearyl alcohol or benzyl alcohol, etc.; synthetic cellulose derivatives such as methyl cellulose, carboxy methylcellulose, ethyl cellulose, hydroxypropylmethyl cellulose, etc.; and other additives conventionally used, such as water, gelatin, talc, vegetable oils, gum arabic, etc.

In general, these capsule, tablet, granule and powder preparations contain the effective ingredient in an amount of 0.1 to 100 wt %, preferably 1 to 100 wt %.

The liquid preparation is prepared in the form of a suspension, syrup or injection, using appropriate additives generally used in liquid preparations, using water, alcohols or vegetable oils such as soybean oil, peanut oil or sesame oil, etc.

As suitable solvents in the case of parenteral administration such as intramuscular injection, intravenous injection or subcutaneous injection, there are, for example, distilled water for injection, Lidocaine hydrochloride solution (for intramuscular injection), physiological saline, glucose aqueous solution, ethanol, liquid for intravenous injection (for example, aqueous solution of citric acid and sodium citrate, etc.) or electrolyte solution (for drip injection and intravenous injection), etc. or a mixture thereof.

These injections may be previously dissolved or may also be in such a form that they are provided in the form of powders by adding appropriate additives thereto and are dissolved upon use. These injections contain the effective ingredient generally in the range of 0.005 to 10 wt %, preferably in the range of 0.05 to 5 wt %.

The liquid preparation for oral administration such as a suspension or syrup contains the effective ingredient in the range of 0.1 to 50 wt %.

The dose of the anti-arrhythmic, anti-myocardial infarction or anti-angina pectoris agent of the present invention may vary depending upon age, health state, body weight or conditions of the patient but its daily dose is in the range of 0.01 to 1 mg/kg for parenteral administration and in the range of 0.1 to 10 mg/kg for oral administration, for adult.

Hereafter the present invention is described in more detail by referring to the examples but is not deemed to limited thereto.

REFERENTIAL EXAMPLE 1

Preparation of 2-formyl-6,7-dimethoxy-1-(4-methoxybenzyl)-1,2,3,4-tetrahydroisoquinolin-8-ol (intermediate 1)

To a suspension of 6,7-dimethoxy-1-(4-methoxybenzyl)-1,2,3,4-tetrahydroisoquinolin-8-ol (2.26 g, 6.86 mmole) in chloroform (60 ml) was added formic trimethylacetic anhydride (1.16 g, 8.91 mmole) at 0° C. The mixture was stirred for 30 minutes and concentrated under reduced pressure. The residue was recrystallized from ethyl acetate-hexane to give intermediate 1 (2.23 g) as colorless crystals.

m.p.: 171°–173° C.
FAB-MS(m/z, $(C_{20}H_{23}NO_5+H)^+$): 358

Intermediates 2~10 (Referential Examples 2~10) were prepared using the corresponding 1,2,3,4-tetrahydroisoquinoline derivatives, according to the reaction in Referential Example 1.

REFERENTIAL EXAMPLE 2

2-Formyl-6,7-dimethoxy-1-(3-methoxybenzyl)-1,2,3,4-tetrahydroisoquinolin-8-ol (intermediate 2)

m.p.: 163°–167° C.
FAB-MS(m/z, $(C_{20}H_{23}NO_5+H)^+$): 358

REFERENTIAL EXAMPLE 3

2-Formyl-6,7-dimethoxy-1-(2-methoxybenzyl)-1,2,3,4-tetrahydroisoquinolin-8-ol (intermediate 3)

m.p.: 156°–157° C.
FAB-MS(m/z, $(C_{20}H_{23}NO_5+H)^+$): 358

REFERENTIAL EXAMPLE 4

2-Formyl-6,7-dimethoxy-1-(3,4-dimethoxybenzyl)-1,2,3,4-tetrahydroisoquinolin-8-ol (intermediate 4)

m.p.: 155°–157° C.
FAB-MS(m/z, $(C_{21}H_{25}NO_4+H)^+$): 388

REFERENTIAL EXAMPLE 5

2-Formyl-6,7-dimethoxy-1-(2,5-dimethoxybenzyl)-1,2,3,4-tetrahydroisoquinolin-8-ol (intermediate 5)

m.p.: 143.0°–144.5° C.
FAB-MS(m/z, $(C_{21}H_{25}NO_6+H)^+$): 388

REFERENTIAL EXAMPLE 6

2-Formyl-6,7-dimethoxy-1-(3,4,5-trimethoxybenzyl)-1,2,3,4-tetrahydroisoquinolin-8-ol (intermediate 6)

m.p.: 190°–195° C.
FAB-MS(m/z, $(C_{22}H_{27}NO_7+H)^+$): 418

REFERENTIAL EXAMPLE 7

2-Formyl-6,7-dimethoxy-1-(3-pyridylmethyl)-1,2,3,4-tetrahydroisoquinolin-8-ol (intermediate 7)

m.p.: 199°–200° C.
FAB-MS(m/z, $(C_{18}H_{20}N_2O_4+H)^+$): 329

REFERENTIAL EXAMPLE 8

2-Formyl-6,7-dimethoxy-1-(4-methoxyphenethyl)-1,2,3,4-tetrahydroisoquinolin-8-ol (intermediate 8)

m.p.: 151.0°–152.5° C.
FAB-MS(m/z, $(C_{21}H_{25}NO_5+H)^+$): 372

REFERENTIAL EXAMPLE 9

2-Formyl-1-(3-methoxybenzyl)-6,7-methylenedioxy-1,2,3,4-tetrahydroisoquinolin-8-ol (intermediate 9)

m.p.: 205°–207° C.
FAB-MS(m/z, $(C_{19}H_{19}NO_5+H)^+$): 342

REFERENTIAL EXAMPLE 10

2-Formyl-6,7-dimethoxy-1-(3,5-dimethoxybenzyl)-1,2,3,4-tetrahydroisoquinolin-8-ol (intermediate 10)

m.p.: 176.5°–178.0° C.
FAB-MS(m/z, $(C_{21}H_{25}NO_6+H)^+$): 388

REFERENTIAL EXAMPLE 11

(1) Preparation of (−)-6,7-dimethoxy-1-(4-methoxybenzyl)-1,2,3,4-tetrahydroisoquinolin-8-ol (−)-6,7-Dimethoxy-1-(4-methoxybenzyl)-1,2,3,4-tetrahydroisoquinolin-8-ol (+)-dibenzoyl-D-tartrate was obtained from (±)-6,7-dimethoxy-1-(4-methoxybenzyl)-1,2,3,4-tetrahydroisoquinolin-8-ol and (+)-dibenzoyl-D-tartaric acid by a conventional method. The salt was purified by repeated recrystallizations from chloroform-acetone-methanol (10:6:1).

m.p.: 173.0°–174.0° C. (dec)

Optical Rotation: $[\alpha]_D^{25} = +58.3°$ (C=0.336, methanol)

The salt was treated with a saturated aqueous sodium hydrogencarbonate solution to give the captioned compound as colorless crystals.

Optical Rotation: $[\alpha]_D^{25} = -15.8°$ (C=0.419, chloroform)

(2) Preparation of (+)-6,7-dimethoxy-1-(4-methoxybenzyl)-1,2,3,4-tetrahydroisoquinolin-8-ol The combined mother liquors of recrystallization in the above (1) were concentrated and the residue was treated with a saturated aqueous sodium hydrogen-carbonate solution to give crude (+)-6,7-dimethoxy-1-(4-methoxybenzyl)-1,2,3,4-tetrahydroisoquinolin-8-ol. The compound was treated with (−)-dibenzoyl-L-tartaric acid to give (+)-6,7-dimethoxy-1-(4-methoxybenzyl)-1,2,3,4-tetrahydroisoquinolin-8-ol (2)-dibenzoyl-L-tartrate. The salt was purified by repeated recrystallizations from chloroform-acetone-methanol (10:6:1).

m.p.: 172.0°–173.0° C. (dec)

Optical Rotation: $[\alpha]_D^{25} = -65.6°$ (C=0.308, methanol)

The salt was treated with a saturated aqueous sodium hydrogencarbonate solution to give the captioned compound as colorless crystals.

Optical Rotation: $[\alpha]_D^{25} = +16.6°$ (C=0.445 chloroform)

EXAMPLE 1

(1) Preparation of Compound 1

Intermediate 1 obtained in Referential Example 1 (360 mg, 1.01 mmole) was dissolved in dimethyl sulfoxide (6 ml), and potassium hydroxide (245 mg, 3.71 mmole, 85%) was added, and the reaction mixture was stirred under nitrogen at room temperature for 5 minutes. To the mixture was added dropwise a solution of 3-chloromethyl-N,N-dimethylbenzylamine hydrochloride (267 mg, 1.21 mmole) in dimethyl sulfoxide (6 ml) over a period of 1 hour, and the mixture was stirred at room temperature for 4 hours. The reaction mixture was diluted with ethyl acetate and washed successively with water and brine. The organic layer was dried over MgSO$_4$ and concentrated under reduced pressure. The residue was purified by MPLC (Merck, Lichroprep Si 60/chloroform:methanol=40:1–10:1) to give the captioned compound (420mg) as a colorless oil.

IR(neat, cm$^{-1}$): 2944,1677,1611,1515,1431,1344,1248, 1179,1122,1086,1632,753

FAB-MS(m/z, (C$_{30}$H$_{36}$N$_2$O$_5$+H)$^+$): 505

$^1$H-NMR(300 MHz, CDCl$_3$, δ ppm): 2.21+2.27(6H,s×2),2.65(1H,dd,J=10.7 Hz,13.7 Hz), 2.70–2.91(2H,m),3.07(1H,dd,J=2.5 Hz,13.7 Hz),3.10–3.29+4.41(2H,m+ddd,J=2.1 Hz,6.7 Hz,13.2 Hz), 3.39+3.44+3.48–3.52(2H,d×2+m,J=13.5 Hz, J=13.5 Hz),3.74+3.75(3H,s×2),3.86+3.88(3H,s×2), 3.93(3H,s),4.30+5.73(1H,dd×2,J=2.5 Hz,10.7 Hz, J=3.4 Hz,9.0 Hz),5.11(1H,d,J=10.9 Hz),5.28+5.35(1H, d×2,J=10.9 Hz,J=10.9 Hz),6.39+6.46(1H,s×2),6.64–6.87(4H,m),7.19(1H,s),7.-30–7.39+7.46–7.52(3H,m×2),7.41+7.97(1H,s×2)

(2) Preparation of Compound 1 hydrochloride

Compound 1 was dissolved in methanol containing hydrogen chloride. The mixture was concentrated under reduced pressure, and the residue was recrystallized from a mixture of methanol and diethyl ether to give the captioned compound as a colorless powder.

m.p.: 161°–167° C.

High Resolution FAB-MS(m/z, (C$_{30}$H$_{36}$N$_2$O$_5$+H)$^+$): Calcd.: 505.2702. Found: 505.2719.

Compounds 2~6 (Examples 2~6) were prepared by the reaction of intermediate 1 (Referential Example 1) with the corresponding chlorides, N-(3-chloromethylbenzyl)pyrrolidine hydrochloride, N-(3-chloromethylbenzyl)morpholine hydrochloride, 4-chloromethyl-N,N-dimethylbenzylamine hydrochloride, N-(3-chloromethylbenzyl)-N'-methylpiperazine dihydrochloride, N-(3-chloropropyl)-N-methylbenzylamine hydrochloride, in the same manner as described in Example 1-(1).

EXAMPLE 2

Compound 2 appearance: colorless oil

IR(neat, cm$^{-1}$): 2938,1674,1611,1515,1431,1344,1245, 1122,1083,1032,753

High Resolution FAB-MS(m/z, (C$_{32}$H$_{38}$N$_2$O$_5$+H)$^+$): Calcd.: 531.2859. Found: 531.2889.

$^1$H-NMR(300 MHz, CDCl$_3$, δ ppm): 1.57(2H,brs),1.75(2H,brs),2.46(4H,brs),2.64(1H, dd,J=10.6 Hz,13.5 Hz),2.66–2.91(2H,m),3.07(1H,dd, J=2.7 Hz,13.5 Hz),3.13(1H,ddd,J=5.4 Hz,11.2 Hz, 13.3 Hz),3.46–3.72(2H,m),3.75(3H,s),3.88(3H,s), 3.93(3H,s),4.29+5.69–5.77(1H,dd+m,J=2.7 Hz, 10.6 Hz),4.40(1H,ddd,J=2.5 Hz,6.4 Hz,13.3 Hz),5.11 (1H,d,J=11.3 Hz),5.24–5.31+5.34(1H,m+d,J=11.3 Hz), 6.39+6.45(1H,s×2),6.64–6.76(4H,m),7.17(1H,s), 7.34(3H,m),7.41+7.97(1H,s×2)

EXAMPLE 3

Compound 3 appearance: colorless oil

FAB-MS(m/z, (C$_{32}$H$_{38}$N$_2$O$_6$+H)$^+$): 547

IR(neat, cm$^{-1}$): 2938,1677,1608,1518,1458,1431,1269, 1179,1119,1083,1032,1008

$^1$H-NMR(300 MHz, CDCl$_3$, δ ppm): 2.38+2.41–2.47(4H,t+m,J=4.7 Hz),2.64(1H,dd, J=10.7 Hz,13.5 Hz),2.72–2.90(2H,m),3.06(1H,dd, J=2.8 Hz,13.5 Hz),3.10–3.30+4.40(2H,m+ddd,J=2.5 Hz, 4.0 Hz,13.0 Hz),3.44+3.48(2H,d×2,J=13.5 Hz, J=13.5 Hz),3.64+3.65–4.00(4H,t+m,J=4.7 Hz),3.74+3.75 (3H,s×2),3.86+3.88(3H,s×2),3.93(3H,s), 4.28+5.72(1H,dd×2,J=2.5 Hz,10.8 Hz,J=4.2 Hz, 10.8 Hz),5.13(1H,d,J=11.3 Hz),5.26+5.33(1H,d×2, J=11.3 Hz,J=11.3 Hz),6.39+6.46(1H,s×2),6.67–6.85

(4H,m),7.17(1H,s),7.33–7.37(3H,m),7.38+7.97(1H,s×2)

EXAMPLE 4

Compound 4 appearance: pale yellow oil
High Resolution FAB-MS(m/z, ($C_{30}H_{36}N_2O_5$+H)$^+$): Calcd.: 505.2702. Found: 505.2719.

$^1$H-NMR(300 MHz, CDCl$_3$, δ ppm): 2.25+2.28(6H,s×2),2.66(1H,dd,J=10.7 Hz,13.9 Hz), 2.71–2.92(2H,m),3.08(1H,dd,J=2.7 Hz,13.9 Hz),3.13–3.30(1H,m),3.46+3.49(2H,s×2),3.74+3.75(3H,s×2),3.86+3.88(3H,s×2),3.93(3H,s),4.35+5.70–5.77 (1H,dd+m,J=2.7 Hz,10.7 Hz),4.36–4.45(1H,m),5.11+5.12(1H,d×2,J=11.1 Hz,J=11.1 Hz),5.24+5.33(1H,d×2,J=11.1 Hz,J=11.1 Hz),6.39+6.46(1H,s×2),6.67–6.90(4H,m),7.22+7.97(1H,s×2),7.34(2H,d, J=8.2 Hz),7.42(2H,d,J=8.2 Hz)

EXAMPLE 5

Compound 5 appearance: colorless oil
IR(neat, cm$^{-1}$): 2938,2800,1677,1518,1497,1458,1428, 1248,1122,1083,1032,825,753
High Resolution FAB-MS(m/z, ($C_{33}H_{41}N_3O_5$+H)$^+$): Calcd.: 560.3124. Found: 560.3134.

$^1$H-NMR(300 MHz, CDCl$_3$, δ ppm): 2.22–2.56(8H,m),2.27(3H,s),2.64(1H,dd,J=10.6 Hz, 14.0 Hz),2.72(1H,ddd,J=2.2 Hz,5.3 Hz,16.8 Hz),2.85 (1H,ddd,J=6.3 Hz,10.9 Hz,16.8 Hz),3.06(1H,dd, J=2.6 Hz,14.0 Hz),3.14(1H,ddd,J=5.3 Hz,10.9 Hz, 12.8 Hz),3.21–3.31+4.40(1H,m+ddd,J=2.2 Hz,6.3 Hz, 12.8 Hz),3.40–3.56(2H,m),3.75(3H,s),3.88(3H,s), 3.93(3H,s),4.29+5.69–5.75(1H,dd+m,,J=2.6 Hz, 10.6 Hz),5.12(1H,d,J=11.1 Hz),5.22–5.28+5.33(1H, m+d,J=11.1 Hz),6.39+6.46(1H,s×2),6.64–6.86(4H, m),7.18(1H,s),7.24–7.51(3H,m),7.38+7.97(1H,s×2)

EXAMPLE 6

Compound 6 appearance: colorless oil
IR(neat, cm$^{-1}$): 2944,2840,2796,1676,1606,1586,1516, 1498,1458,1432,1248,1122,1034,738
FAB-MS(m/z, ($C_{31}H_{38}N_2O_5$+H)$^+$): 519

$^1$H-NMR(300 MHz, CDCl$_3$, δ ppm): 2.06–2.15(2H,m),2.24+2.25(3H,s×2),2.65(2H,brt, J=7.3 Hz),2.76(1H,dd,J=10.5 Hz,13.9 Hz),2.70–2.92 (2H,m),3.14(1H,dd,J=2.8 Hz,13.9 Hz),3.17–3.25(1H, m),3.54(2H,s),3.75+3.77(3H,s×2),3.84(3H,s),3.85 (3H,s),4.14–4.21(1H,m),4.34–4.48(2H,m),4.62+5.73 (1H,dd×2,J=2.8 Hz,10.5 Hz,J=4.2 Hz,9.8 Hz),6.35+6.42 (1H,s×2),6.75–6.85(2H,m),7.00–7.07(2H,m), 7.22–7.33(5H,m),7.51+8.00(1H,s×2)

Compounds 7~12 (Examples 7~12) were prepared by the reaction of intermediate 2 (Referential Example 2) with the corresponding chlorides, 3-chloromethyl-N,N-dimethylbenzylamine hydrochloride, 4-chloromethyl-N,N-dimethylbenzylamine hydrochloride, 3-chloromethyl-4-methoxy-N,N-dimethylbenzylamine hydrochloride, N-(3-chloromethylbenzyl)morpholine hydrochloride, 2-chloromethylpyridine hydrochloride, 3-chloromethylpyridine hydrochloride in the same manner as described in Example 1-(1).

EXAMPLE 7

Compound 7 appearance: pale yellow oil
IR(neat, cm$^{-1}$): 3466,2776,1605,1497,1437,1344,1236, 1122,1032,800,703
High Resolution FAB-MS (m/z, ($C_{30}H_{36}N_2O_5$+H)$^+$): Calcd.: 505.2702. Found: 505.2730.

$^1$H-NMR(300 MHz, CDCl$_3$, δ ppm): 2.22+2.29(6H,s×2),2.70(1H,dd,J=10.7 Hz,13.8 Hz ), 2.68–2.91(2H,m),3.12(1H,dd,J=2.8 Hz,13.8 Hz),3.11–3.18(1H,m),3.42(1H,d,J=13.1 Hz ),3.48(1H,d, J=13.1 Hz),3.67+3.70(3H,s×2),3.86+3.88(3H,s×2), 3.92(3H,s),4.35–4.42(2H,m),5.11+5.14(1H,d×2, J=10.1 Hz ,J=11.2 Hz ),5.28+5.33(1H,d×2,J=10.1 Hz, J=11.2 Hz),6.40+6.46(1H,s×2),6.44+6.46(1H,s×2), 6.69–6.72(1H,m),7.07–7.10(1H,m),7.23(1H,s),7.29–7.47(4H,m),7.39+7.92(1H,s×2)

EXAMPLE 8

Compound 8 appearance: colorless oil
IR(neat, cm$^-$): 2944,2776,1677,1605,1584,1497,1458, 1437,1122,1083,1035,966
High Resolution FAB-MS(m/z, ($C_{30}H_{36}N_2O_5$+H)$^+$): Calcd.: 505.2702. Found: 505.2713.

$^1$H-NMR(300 MHz, CDCl$_3$, δ ppm): 2.24+2.28(6H,s×2),2.71(1H,dd,J=10.7 Hz,13.8 Hz), 2.70–2.89(2H,m),3.13(1H,dd,J=2.8 Hz,13.8 Hz),3.12–3.20(1H,m),3.46(2H,brs),3.68+3.71(3H,s×2), 3.86+3.88(3H,s×2),3.92(3H,s),4.35–4.43(1H,m), 4.43(1H,dd,J=2.5 Hz,10.7 Hz),5.15(1H,d,J=11.1 Hz), 5.31(1H,d,J=11.1 Hz),6.40+6.44(1H,s×2),6.44–6.59 (2H,m),6.67–6.72(1H,m),7.07–7.13(1H,m),7.29–7.42 (4H,m),7.42+7.98(1H,s×2)

EXAMPLE 9

Compound 9 appearance: colorless oil
IR(neat, cm$^{-1}$): 2944,2776,1674,1605,1584,1500,1461, 1437,1260,1122,1083,1032,756
High Resolution FAB-MS (m/z, ($C_{31}H_{38}N_2O_6$+H)$^+$): Calcd.: 535.2808. Found: 535.2828.

$^1$H-NMR(300 MHz, CDCl$_3$, δ ppm): 2.20+2.30(6H,s×2),2.67(1H,dd,J=10.7 Hz,13.6 Hz), 2.70–2.89(2H,m),3.13(1H,dd,J=2.5 Hz,13.6 Hz),3.10–3.19(1H,m),3.40(2H,brs),3.67+3.71(3H,s×2)-,3.74 (3H,s),3.85+3.87(3H,s×2),3.91+3.95(3H,s×2), 4.36–4.43(1H,m),4.54(1H,dd,J=2.5 Hz,10.7 Hz),5.14 (1H,d,J=10.9 Hz),5.42(1H,d,J=10.9 Hz),6.37+6.43 (1H,s×2),6.43–6.54(2H,m),6.68–6.71(1H,m),8.67 (1H,d,J=8.1 Hz),7.05–7.13(1H,m),7.27–7.29(2H,m), 7.43+7.98(1H,s×2)

EXAMPLE 10

Compound 10 appearance: colorless oil
IR(neat, cm$^{-1}$): 2938,2854,1677,1605,1584,1497,1458, 1434,1269,1119,864,753
High Resolution FAB-MS(m/z, ($C_{32}H_{38}N_2O_6$+H)$^+$): Calcd.: 547.2808. Found: 547.2781.

$^1$H-NMR(300 MHz, CDCl$_3$, δ ppm): 2.37+2.43(4H, brt×2,J=4.6 Hz,J=4.6 Hz),2.69(1H,dd, J=10.9 Hz,13.6 Hz),2.71–3.00(2H,m),3.11(1H,dd, J=2.4 Hz,13.6 Hz),3.10–3.19(1H,m),3.43(1H,d, J=3.2 Hz),3.49(1H, d, J=3.2 Hz),3.64–3.69(4H,m),3.71 (3H,s),3.86+3.88(3H,s×2),3.93(3H,s),4.32–4.42 (2H,m),5.16(1H,d,J=11.3 Hz),5.32(1H,d,J=11.3 Hz), 6.40–6.55(3H,m),6.69–6.72(1H,m),7.07–7.13(1H,m), 7.20(1H,s),7.31–7.38(3H,m),7.38+7.98(1H,s×2)

EXAMPLE 11

Compound 11 appearance: colorless oil
IR(neat, cm$^{-1}$): 2944,1674,1605,1497,1458,1437,1344, 1269,1122,1086,1038,762
High Resolution FAB-MS(m/z, (C$_{26}$H$_{28}$N$_2$O$_5$+H)$^+$): Calcd.: 449.2076. Found: 449.2091.
$^1$H-NMR(300 MHz, CDCl$_3$, δ ppm): 2.76(1H,dd,J=10.9 Hz,13.8 Hz),2.73–2.95(2H,m), 3.14–3.24(2H,m),3.68+3.71(3H,s×2),3.86+3.87(3H, s×2),3.91(3H,s),4.41(1H,ddd,J=2.7 Hz,6.6 Hz, 13.2 Hz),4.71(1H,dd,J=2.8 Hz,10.9 Hz),5.27+5.29(1H, d×2,J=12.1 Hz,J=12.7 Hz),5.40+5.45(1H,d×2, J=12.7 Hz,J=12.1 Hz),6.42+6.47(1H,s×2),6.51–6.59 (2H,m),6.69–6.73(1H,m),7.08–7.14(1H,m),7.26–7.30 (1H,m),7.41+7.99(1H,s×2),7.51–7.54(1H,m),7.-72–7.77(1H,m),S.63–8.65(1H,m)

EXAMPLE 12

Compound 12 appearance: colorless oil
IR(neat, cm$^{-1}$): 2944,1674,1605,1584,1497,1434,1344, 1267,1233,1122,1086,1032
High Resolution FAB-MS(m/z, (C$_{26}$H$_{28}$N$_2$O$_5$+H)$^+$): Calcd.: 449.2076. Found: 449.2077.
$^1$H-NMR(300 MHz, CDCl$_3$, δ ppm): 2.59–2.91(2H,m),2.76(1H,dd,J=10.5 Hz,13.9 Hz),3.10 (1H,dd,J=2.9 Hz,13.9 Hz),3.13–3.29(1H,m),3.69+3.71 (3H,s×2),3.86+3.90(3H,s×2),3.86+3.88(3H,s×2), 4.37–4.45(1H,m),4.47+5.76(1H,dd×2,J=2.9 Hz, 10.5 Hz,J=4.3 Hz,9.2 Hz),5.13+5.20(1H,d×2, J=11.4 Hz,J=11.6 Hz),5.25+5.34(1H,d×2,J=11.4 Hz, J=11.6 Hz),6.43+6.49(1H,s×2),6.51–6.58(2H,m), 6.69–6.74(1H,m),7.09+7.14(1H,t×2,J=7.9 Hz, J=7.8 Hz),7.32–7.38(1H,m),7.37+8.00(1H,s×2), 7.79+7.90–7.94(1H,td+m,J=2.1 Hz,7.8 Hz),8.61–8.64 (1H,m),8.74–8.75(1H,m)

Compounds 13~21 (Examples 13~21) were prepared by the reaction of corresponding intermediates 3~9 (Referential Examples 3~9) with the corresponding chlorides, 3-chloromethyl-N,N-dimethylbenzylamine hydrochloride, N-(3-chloromethylbenzyl)morpholine hydrochloride, (4-chlorobutylthio)benzene, in the same manner as described in Example 1-(1).

EXAMPLE 13

Compound 13 appearance: pale brown oil
IR(neat, cm$^{-1}$): 2944,1674,1605,1500,1464,1434,1344, 1245,1122,1086,1032,753
High Resolution FAB-MS(m/z, (C$_{30}$H$_{36}$N$_2$O$_5$+H)$^+$): Calcd.: 505.2705. Found: 505.2704.
$^1$H-NMR(300 MHz, CDCl$_3$, δ ppm): 2.21+2.27(6H,s×2),2.77–2.83(2H,m),3.23(2H,d, J=6.3 Hz),3.25–3.38(1H,m),3.41(1H,d,J=13.1 Hz), 3.46(1H,d,J=13.1 Hz),3.64+3.67(3H,s×2),3.86+3.88 (3H,s×2),3.86+3.90(3H,s×2),4.23–4.30(1H,m), 4.53(1H,t,J=7.2Hz),5.15(1H,d,J=11.3Hz),5.30(1H, d,J=11.3 Hz),6.41+6.47(1H,s×2),6.72–6.79(3H,m), 7.12–7.18(1H,m),7.29–7.40(5H,m)

EXAMPLE 14

Compound 14 appearance: colorless oil
IR(neat, cm$^{-1}$): 3466,2944,1668,1518,1500,1458,1431, 1269,1239,1122,1029
High Resolution FAB-MS(m/z, (C$_{31}$H$_{38}$N$_2$O$_6$+H)$^+$): Calcd.: 535.2808. Found: 535.2838.
$^1$H-NMR(300 MHz, CDCl$_3$, δ ppm): 2.21+2.29(6H,s×2),2.70(1H,dd,J=10.4 Hz,14.0 Hz), 2.68–2.94(2H,m),3.07(1H,dd,J=2.8 Hz, 14.0 Hz),3.11–3.19(1H,m),3.41(1H,d,J=13.5 Hz),3.45(1H,d, J=13.5 Hz),3.65+3.67(3H,s×2),3.82+3.83(3H,s×2), 3.85+3.88(3H,s×2),3.93(3H,s),4.36–4.43(2H,m), 5.16(1H,d,J=11.5 Hz),5.33(1H,d,J=11.5 Hz),6.46–6.52(3H,m),6.65–6.70(1H,m),7.28–7.50(4H,m), 7.37+8.01(1H,s×2)

EXAMPLE 15

Compound 15 appearance: colorless oil
IR(neat, cm$^{-1}$): 2944,2836,1671,1608,1506,1432,1227, 1122,1083,1032,790,745,695
High-Resolution FAB-MS(m/z, (C$_{31}$H$_{38}$N$_2$O$_6$+H)$^+$): Calcd.: 535.2808. Found: 535.282.
$^1$H-NMR(300 MHz, CDCl$_3$, δ ppm): 2.01+2.28(6H,s×2),2.70–2.91(2H,m),3.01(2H,d, J=7.1 Hz),3.28(1H,ddd,J=6.3 Hz,10.0 Hz,13.4 Hz),3.45 (1H,d,J=13.0 Hz),3.47(1H,d,J=13.0 Hz),3.61+3.63 (3H,s×2),3.63+3.66(3H,s×2),3.85+3.88(3H,s×2), 3.88+3.90(3H,s×2),4.25(1H,ddd,J=3.5 Hz,6.3 Hz, 13.4 Hz),4.54+5.89(1H,t+dd,J=7.1 Hz,J=3.8 Hz, 10.0 Hz),5.17+5.18(1H,d×2,J=11.2 Hz,J=11.2 Hz), 5.27+5.28(1H,d×2,J=11.2 Hz,J=11.2 Hz),6.41+6.46 (1H,s×2),6.47(1H,s),6.60–6.75(2H,m),7.24–7.55 (4H,m),7.38+7.92(1H,s×2)

EXAMPLE 16

Compound 16 appearance: yellow oil
High Resolution FAB-MS(m/z, (C$_{32}$H$_{40}$N$_2$O$_7$+H)$^+$): Calcd.: 565.2914. Found: 565,2920.
$^1$H-NMR(300 MHz, CDCl$_3$, δ ppm): 2.21+2.34(6H,s×2),2.73(1H,dd,J=10.5 Hz,13.9 Hz), 2.79–3.01(2H,m),3.06(1H,dd,J=2.6 Hz,13.9 Hz),3.10–3.27(1H,m),3.43(2H,s),3.68(6H,s),3.78+3.79(-3H,s× 2),3.87+3.88(3H,s×2),3.92(3H,s),4.37–4.48(1H, m),4.41–4.48+5.-75–5.82(1H,m×2),5.11+5.18(1H,d×2,J=11.5 Hz,J=11.5 Hz),5.27+5.32(1H,d×2,J=11.5 Hz, J=11.5 Hz),6.13+6.17(2H,s×2),6.40+6.47(1H,s×2), 7.26–7.55(4H,m),7.39+8.06(1H,s×2)

EXAMPLE 17

Compound 17 appearance: pale yellow oil

IR(neat, cm$^{-1}$): 2944,1674,1497,1458,1434,1344,1122, 1086,1029

High Resolution FAB-MS(m/z, ($C_{28}H_{33}N_3O_4$+H)$^+$): Calcd.: 476.2549. Found: 476.25206.

$^1$H-NMR(300 MHz, CDCl$_3$, δ ppm): 2.18+2.24(6H,s×2),2.60-2.95(2H,m),2.73(1H,dd, J=10.7 Hz,13.9 Hz),3.14(1H,dd,J=2.6 Hz,13.9 Hz), 3.15-3.40(1H,m),3.40+3.47(2H,s×2),3.86+3.88(3H, s×2),3.90+3.94(3H,s×2),4.31+5.71(1H,dd×2, J=2.6 Hz,10.7 Hz,J=2.8 Hz,9.0 Hz),4.38-4.50(1H,m), 5.09+5.13(1H,d×2,J=10.5 Hz,J=10.5 Hz),5.31+5.36 (1H,d×2,J=10.5 Hz,J=10.5 Hz),6.41+6.46(1H,s×2), 7.00-7.61(8H,m),7.60+7.95(1H,s×2)

EXAMPLE 18

Compound 18 appearance: colorless oil

IR(neat, cm$^{-1}$): 2944,2775,1671,1611,1515,1434,1344, 1245,1122,1086,1032,827

High Resolution FAB-MS(m/z, ($C_{31}H_{38}N_2O_5$+H)$^+$): Calcd.: 519.2859. Found: 519.2830.

$^1$H-NMR(300 MHz, CDCl$_3$, δ ppm): 1.78-1.94+2.- 15-2.45(2H,m×2),2.21+2.30(6H,s×2), 2.48-3.11(5H,m),3.43+3.57(2H,s×2),3.75+3.78(3H, s×2),3.82+3.84(3H,s×2),3.83+3.87(3H,s×2), 4.22+5.59(1H,dd×2,J=3.0 Hz,10.9 Hz,J=3.0 Hz, 10.7 Hz),4.40(1H,ddd,J=2.5 Hz,6.8 Hz,12.8 Hz),5.04-5.21(2H,m),6.38+6.40(1H,s×2),6.74+6.77(2- H,d×2, J=8.3 Hz, J=8.8 Hz),6.97+7.00(2H,d×2,J=8.3 Hz, J=8.8 Hz),7.11-7.45(4H,m),7.73+8.22(1H,s×2)

EXAMPLE 19

Compound 19 appearance: colorless oil

IR(neat, cm$^-$): 2944,2780,1674,1479,1440,1389,1263, 1155,1095,1038,695

High Resolution FAB-MS(m/z, ($C_{29}H_{32}N_2O_5$+H)$^+$): Calcd.: 489.2389. Found: 489.2408.

$^1$H-NMR(300 MHz, CDCl$_3$, δ ppm): 2.26+2.32(6H,s×2),2.54-2.92(3H,m),3.06-3.34(2H, m),3.54+3.64(2H,s×2),3.68+3.69(3H,s×2),3.43-3.52- +4.39(1H,m+ddd,J=2.4 Hz,6.3 Hz,13.2 Hz), 4.58+5.81(1H,dd×2,J=10.4 Hz,12.4 Hz,J=3.8 Hz, 9.4 Hz),5.32+5.33(1H,d×2,J=11.4 Hz,J=11.2 Hz), 5.39+5.42(1H,d×2,J=11.4 Hz,J=11.2 Hz),5.92+5.96 (1H,d+s,J=3.0 Hz),5.95+5.96(1H,d+s,J=3.0 Hz), 6.30+6.37(1H,s×2),6.46-6.76(3H,m),7.03-7.50(5H, m),7.40+7.97(1H,s×2)

EXAMPLE 20

Compound 20 appearance: colorless oil

IR(neat, cm$^{-1}$): 2944,2812,1677,1626,1482,1440,1263, 1155,1116,1038,864,753

High Resolution FAB-MS(m/z, ($C_{31}H_{34}N_2O_6$+H)$^+$): Calcd.: 531.2495. Found: 531.2500.

$^1$H-NMR(300 MHz, CDCl$_3$, δ ppm): 2.38(4H,t,J=4.6 Hz),2.51-2.90(3H,m),3.08-3.35(2H, m),3.48(2H,s),3.64(4H,t,J=4.6 Hz),3.65+3.68(3H,s×2),4.39(1H,ddd,J=2.8 Hz,6.6 Hz,13.1 Hz),4.56+5.79 (1H,dd×2,J=2.6 Hz,10.5 Hz,J=4.0 Hz,9.4 Hz),5.30+5.33(1H,d×2,J=11.4 Hz,J=11.3 Hz),5.39+5.42(1H,d×2,J=11.4 Hz,J=11.3 Hz),5.93+5.97(1H,d+s,J=6.3 Hz), 5.94+5.97(1H,d+s,J=6.3 Hz),6.30+6.37(1H,s×2), 6.46-6.76(3H,m),7.10(1H,t,J=8.0 Hz),7.39-7.48(4H, m),7.43+7.96(1H,s×2)

EXAMPLE 21

Compound 21 appearance: pale yellow oil

IR(neat, cm$^{-1}$): 1605,1404,1311,1272,1236,1191,1026, 717,693

High Resolution FAB-MS(m/z, ($C_{28}H_{32}N_2O_4S$+H)$^+$): Calcd.: 493.2161. Found: 493.2151.

$^1$H-NMR(300 MHz, CDCl$_3$, δ ppm): 1.80-2.10(4H,m),2.55-2.65+2.69-2.80(1H,m×2), 2.87(1H,dd,J=10.5 Hz,14.2 Hz),2.80-3.02(1H,m), 3.00-3.10(2H,m),3.22+3.24(1H,dd×2,J=4.2 Hz, 14.2 Hz,J=4.2 Hz,14.2 Hz),3.40-3.62(1H,m),3.81+3.82 (3H,s×2),3.84+3.85(3H,s×2),4.00-4.16(1H,m), 4.20-4.40(1H,m),4.46(1H,ddd,J=2.4 Hz,6.9 Hz, 13.2 Hz),4.67+5.71(1H,dd×2,J=4.2 Hz,10.5 Hz, J=4.2 Hz,10.8 Hz),6.38+6.43(1H,s×2),7.12-7.56(7H, m),7.60+7.99(1H,s×2),8.26+8.45(1H,d,J=1.8 Hz, J=1.8 Hz),8.44+8.51(1H,dd,J=1.8 Hz,4.9 Hz,J=1.8 Hz, 4.9 Hz)

EXAMPLE 22

(1) Preparation of 8-(3-chloromethylbenzyloxy)-2-formyl-6,7-dimethoxy-1-(3-methoxybenzyl)-1,2,3,4-tetrahydroisoquinoline To a suspension of sodium hydride (80 mg, 1.96 mmole, 60%) in dimethyl sulfoxide (1 ml) was added a solution of intermediate 2 obtained in Referential Example 2 (350 mg, 0.98 mmole) at room temperature under nitrogen, and the reaction mixture was stirred for 10 minutes. The resulting mixture was added dropwise to a solution of α,α'-dichloro-m-xylene (172 mg, 0.98 mmole) in dimethyl sulfoxide (1 ml) at room temperature, and stirred for 2 hours. The reaction mixture was chilled in ice, diluted with water, and extracted with ethyl acetate. The combined organic layers were dried over MgSO$_4$, and concentrated under reduced pressure. The residue was purified by column chromatography (silica gel/ethyl acetate) to give the desired compound (387 mg) as a pale yellow oil.

FAB-MS(m/z, ($C_{28}H_{30}NO_5Cl$+H)$^+$): 496

(2) Preparation of Compound 22

The compound obtained in (1) (64.0 mg, 0.129 mmole) was treated with a 40% solution of methylamine in methanol (2 ml), and stirred at room temperature for 4 hours. The mixture was evaporated under reduced pressure, and the residue was purified by preparative thin-layer chromatography (Merck, silica gel 60F$_{254}$ chloroform:methanol=10:1) to give the captioned compound (51.2 mg) as a pale yellow oil.

IR(neat, cm$^{-1}$): 2938,2794,1674,1605,1584,1497,1458, 1437,1377,1344,1269,1236,1191,1151, 1122,1083,1032,1005,963,753,699

High Resolution FAB-MS(m/z, ($C_{29}H_{34}N_2O_5$+H)$^+$): Calcd.: 491.2546. Found: 491.2540.

$^1$H-NMR(300 MHz, CDCl$_3$, δ ppm): 2.42+2.53(3H,s×2),2.63-2.91(3H,m),3.07-3.20(2H, m),3.53-3.60+4.34-4.42(1H,m×2),3.70+3.73(3H,s×2- ),3.88(2H,s),3.81+3.87(3H,s×2),3.92+3.96(3H,s×2),4-

.34–4.42+5.37–5.42(1H,m×2),5.05+5.14(1H,d×2,J=11.3 Hz,J=11.3 Hz),5.33+5.42(1H,d×2, J=11.3 Hz,J=11.3 Hz),6.35–6.50(3H,m),6.68–6.74(1H,m),7.08–7.17(1H,m),7.30–7.45(4H,m),7.47+7.78(1H, s×2)

Compounds 23~25 (Examples 23~25) were prepared by the reaction of the compound obtained in Example 22-(1) with the corresponding amines, N-methylpiperazine, thiomorpholine, 1,3-thiazolidine, in the same manner as described in Example 22-(2). Compounds 26~29 were prepared using intermediate 2 obtained in Referential Example 2, α,α'-dichloro-o-xylene and dimethylamine (Example 26); intermediate 1 obtained in Referential Example 1, α,α'-dichloro-o-xylene and dimethylamine (Example 27); intermediate 1, α,α'-dichloro-m-xylene and N-methylethanolamine (Example 28); intermediate 10 obtained in Referential Example 10, α,α'-dichloro-o-xylene and dimethylamine (Example 29), in the same manner as described in Example 22.

EXAMPLE 23

Compound 23 appearance: pale yellow oil

IR(neat, cm$^{-1}$): 2938,2800,1677,1605,1584,1497,1461, 1437,1374,1344,1269,1236,1188,1167, 1122,1086,1035,1014,978,963,825, 753,699

High Resolution FAB-MS(m/z, ($C_{33}H_{41}N_3O_5$+H)$^+$): Calcd.: 560.3124. Found: 560.3143.

$^1$H-NMR(300 MHz, CDCl$_3$, δ ppm): 2.29+2.31(3H,s×2),2.32–2.56(8H,m),2.69(1H,dd, J=11.0 Hz,14.0 Hz),2.74–2.91(2H,m),3.11(1H,dd, J=3.0 Hz,14.0 Hz),3.10–3.20(1H,m),3.47+3.54(2H,s×2),3.70+3.73(3H,s×2),3.86+3.88(3H,s×2),3.93 (3H,s),4.30–4.42(1H,m),4.36+5.76–5.82(1H,dd+m, J=3.0 Hz,11.0 Hz),5.12+5.14(1H,d×2,J=11.2 Hz, J=11.2 Hz),5.26+5.32(1H,d×2,J=11.2 Hz,J=11.2 Hz), 6.40–6.58(3H,m),6.68–6.73(1H,m),7.09+7.10(1H,t×2,J=8.0 Hz,J=8.0 Hz),7.20–7.50(4H,m),7.37+7.98(1H, s×2)

EXAMPLE 24

Compound 24 appearance: pale brown oil

IR(neat, cm$^{-1}$): 2938,1677,1605,1584,1497,1458,1434, 1371,1344,1266,1236,1191,1155,1122, 1083,1035,1005,963,798,753,699

High Resolution FAB-MS(m/z, ($C_{32}H_{38}N_2O_5S$+H)$^+$): Calcd.: 563.2579. Found: 563.2597.

$^1$H-NMR(300 MHz, CDCl$_3$, δ ppm): 2.55–2.91(11H,m),2.69(1H,dd,J=11.0 Hz,13.8 Hz), 3.11(1H,dd,J=3.0 Hz,13.8 Hz),3.47+3.54(2H,s×2), 3.67+3.70(3H,s×2),3.86+3.88(3H,s×2),3.93(3H, s),4.34+5.75–5.81(1H,dd+m,J=3.0 Hz,11.0 Hz),4.35–4.42(1H,m),5.12+5.16(1H,d×2,J=11.2 Hz,J=11.2 Hz), 5.26+5.32(1H,d×2,J=11.2 Hz,J=11.2 Hz),6.39–6.57 (3H,m),6.65–6.73(1H,m),7.06+7.10(1H,t×2, J=7.7 Hz,J=7.7 Hz),7.19–7.48(4H,m),7.35+7.98(1H,s×2)

EXAMPLE 25

Compound 25 appearance: pale yellow oil

IR(neat, cm$^{-1}$): 2944,1674,1605,1563,1497,1434,1374, 1344,1266,1233,1155,1122,1083,1044

High Resolution FAB-MS(m/z, ($C_{31}H_{36}N_2O_5S$+H)$^+$): Calcd.: 549.2423. Found: 549.2443.

$^1$H-NMR(300 MHz, CDCl$_3$, δ ppm): 2.70(1H,dd,J=10.7 Hz,13.6 Hz),2.74–3.20(7H,m),3.11 (1H,dd,J=2.0 Hz,13.6 Hz),3.52+3.58(2H,s×2),3.67+3.71(3H,s×2),3.86+3.88(3H,s×2),3.93(3H,s), 3.96+4.04(2H,s×2),4.33–4.43+5.74–5.80(2H,m×2), 5.13+5.16(1H,d×2,J=11.2 Hz,J=11.2 Hz),5.27+5.33 (1H,d×2,J=11.2 Hz,J=11.2 Hz),6.39–6.56(3H,m), 6.66–6.74(1H,m),7.09+7.10(1H,t×2,J=8.0 Hz, J=8.0 Hz),7.20–7.23(1H,m),7.33–7.42(3H,m),7.44+7.97(1H,s×2)

EXAMPLE 26

Compound 26 appearance: colorless powder m.p.: 126°–128° C.

IR(neat, cm$^{-1}$): 1677,1605,1458,1434,1122,1086,1032

High Resolution FAB-MS(m/z, ($C_{30}H_{36}N_2O_5$+H)$^+$): Calcd.: 505.2702. Found: 505.2716.

$^1$H-NMR(300 MHz, CDCl$_3$, δ ppm): 2.18+2.21(6H,s×2),2.72(1H,dd,J=11.0 Hz,13.6 Hz), 2.80–2.95(1H,m),3.11(1H,dd,J=2.8 Hz,13.6 Hz),3.10–3.24(1H,m),3.38(1H,d,J=12.8 Hz),3.57(1H,d, J=12.8 Hz),3.40–3.60(1H,m),3.65+3.66(3H,s×2), 3.87+3.89(3H,s×2),3.87+3.92(3H,s×2),4.34–4.46+5.79(2H,m+dd,J=3.0 Hz,6.7 Hz),5.22+5.24(1H,d×2, J=11.8 Hz,J=11.8 Hz),5.47+5.57(1H,d×2,J=11.8 Hz, J=11.8 Hz),6.37(1H,d,J=7.5 Hz),6.40(1H,d,J=2.4 Hz), 6.47(1H,s),6.69(1H,dd,J=2.4 Hz,7.5 Hz),7.08(1H,t, J=7.5 Hz),7.30–7.41(3H,m),7.50–7.58(1H,m), 7.36+7.98(1H,s×2)

EXAMPLE 27

Compound 27 appearance: colorless oil

IR(neat, cm$^{-1}$): 2938,2860,2770,1674,1611,1515,1458, 1434,1248,1179,1122,1032,843,756

High Resolution FAB-MS(m/z, ($C_{30}H_{36}N_2O_5$+H)$^+$): Calcd.: 505.2702. Found: 505.2725.

$^1$H-NMR(300 MHz, CDCl$_3$, δ ppm): 2.20+2.25(6H,s×2),2.66(1H,dd,J=10.7 Hz,13.9 Hz), 2.70–2.84(2H, m),3.05(1H,dd,J=2.9 Hz,13.9 Hz),3.16 (1H,ddd,J=5.4 Hz,10.9 Hz,13.2 Hz),3.42(1H,d, J=13.1 Hz),3.62(1H,d,J=13.1 Hz),3.74+3.75(3H,s×2),3.87+3.89(3H,s×2),3.93(3H,s),4.33+5.70(1H,dd×2,J=2.9 Hz,10.7 Hz,J=2.9 Hz,10.7 Hz),4.40(1H,ddd, J=2.4 Hz,6.3 Hz,13.2 Hz),5.21(1H,d,J=11.7 Hz), 5.46+5.59(1H,d×2,J=11.5 Hz,J=11.7 Hz),6.41+6.47 (1H,s×2),6.61–6.83(4H,m),7.27–7.72(4H,m), 7.22+7.98(1H,s×2)

EXAMPLE 28

Compound 28 appearance: pale yellow oil

IR(neat, cm$^{-1}$): 1668,1516,1498,1456,1432,1248,1122, 1084,1032

High Resolution FAB-MS(m/z, $(C_{31}H_{38}N_2O_6+H)^+$): Calcd.: 535.2808. Found: 535.2829.

$^1$H-NMR(300 MHz, CDCl$_3$, δ ppm): 2.17+2.28(3H,s×2),2.56(2H,t,J=5.3 Hz),2.65(1H, dd,J=10.8 Hz,13.9 Hz),2.50–2.92(2H,m),3.05(1H,dd, J=2.6 Hz,13.9 Hz),3.05–3.28(1H,m),3.55+3.56(2H,s×2),3.60(2H,t,J=5.3 Hz),3.74+3.76(3H,s×2),3.86+3.88(3H,s×2),3.90+3.94(3H,s×2),4.26+5.70(1H,dd×2,J=2.6 Hz,10.8 Hz,J=4.3 Hz,13.5 Hz),4.39(1H,ddd, J=2.3 Hz,6.4 Hz,13.1 Hz),5.08+5.13(1H,d×2, J=10.7 Hz,J=11.1 Hz),5.30+5.33(1H,d×2,J=10.7 Hz, 11.1 Hz),6.40+6.46(1H,s×2),6.65–6.83(4H,m),7.16 (1H,s),7.29–7.41(3H,m),7.38+7.96(1H,s×2)

EXAMPLE 29

Compound 29 appearance: colorless oil

IR(neat, cm$^{-1}$): 2944,2776,1677,1602,1467,1434,1344, 1206,1155,1122,840,753

High Resolution FAB-MS(m/z, $(C_{31}H_{38}N_2O_6+H)^+H$): Calcd.: 535.2808. Found: 535.2833.

$^1$H-NMR(300 MHz, CDCl$_3$, δ ppm): 2.17+2.22(6H,s×2),2.70(1H,dd,J=10.8 Hz,13.6 Hz), 2.72–2.92(2H,m),3.09(1H,dd,J=2.8 Hz,13.6 Hz),3.13–3.21(1H,m),3.38(1H,d,J=12.8 Hz),3.54(1H,d, J=12.8 Hz),3.63(6H,s),3.88(3H,s),3.91(3H,s),4.33–4.41(1H,m),- 4.45(1H,dd,J=2.8 Hz,10.8 Hz),5.22+5.27 (1H,d×2,J=11.7 Hz,J=12.2 Hz),6.04+6.13(2H,d×2, J=2.2 Hz,J=2.1 Hz),6.24–6.26(1H,m),6.42+6.47(1H,s×2),7.28–7.34(4H,m),7.35+8.00(1H,s×2),7.53–7.56(1H,m)

EXAMPLE 30

(1) Preparation of 6,7-dimethoxy-8-(3-dimethylaminomethylbenzyloxy)-1-(4-methoxybenzyl)-1,2,3,4-tetrahydroisoquinoline To a solution of compound 1 obtained in Example 1 (268 mg, 0.531 mmole) in ethanol (4.6 ml) was added a solution of sodium hydroxide (500 mg, 12.5 mole) in water (0.6 ml), and the reaction mixture was refluxed under an argon atmosphere for 22 hours. The reaction mixture was diluted with water, and extracted with ethyl acetate. The combined organic layers were washed with brine, dried over MgSO$_4$, and concentrated under reduced pressure to give the desired compound (213 mg) as a yellow oil.

FAB-MS(m/z, $(C_{29}H_{36}N_2O_4+H)^+$): 477

(2) Preparation of Compound 30

To a solution of the compound obtained in (1) (250 mg, 0.525 mmole) in dichloromethane (7 ml) were sequentially added hydroxyacetic acid (44 mg, 0.578 mmole), HOBt (78 mg, 0.577 mmole), and at 0° C. EDCI (111 mg, 0.579 mmole), then the mixture was stirred under nitrogen at 0° C. for 3.5 hours. To the mixture were added hydroxyacetic acid (34 mg, 0.447 mmole) and EDCI (82 mg, 0.428 mmole), and the reaction mixture was stirred at 0° C. for 1.5 hours. The resulting mixture was roughly purified by dry column flash chromatography (silica gel/chloroform:methanol=10:1), and purified by preparative thin-layer chromatography (Merck, silica gel 60F$_{254}$/chloroform:methanol=10:1) to give the captioned compound (182 mg) as a colorless oil.

IR(neat, 2944,1647,1611,1515,1500,1458,1344, 1248,1122,1083,1032

High Resolution FAB-MS(m/z, $(C_{31}H_{38}N_2O_6+H)^+$): Calcd.: 535.2808. Found: 535.2820.

$^1$H-NMR(300 MHz, CDCl$_3$, δ ppm): 2.31+2.46(6H,s×2),2.70(1H,d,J=15.0 Hz),2.65–3.51 (5H,m),3.43(1H,d,J=15.0 Hz),3.58+3.80(2H,s×2), 3.75(3H,s),3.86+3.88(3H,s×2),3.88+3.93(3H,s×2),4.40+5.86(1H,dd×2,J=1.8 Hz,10.7 Hz,J=5.4 Hz, 8.3 Hz),4.65–4.75(1H,m),5.05+5.08(2H,d×2, J=11.1 Hz,J=11.1 Hz),5.24+5.41(1H,d×2,J=11.1 Hz, J=11.1 Hz),6.40+6.45(1H,s×2),6.63–6.78(4H,m), 7.40–7.55(4H,m)

Compounds 31~33 (Examples 31~33) were prepared by the condensation of the compound obtained in Example 30-(1) with the corresponding carboxylic acids, 3-hydroxypropionic acid, DL-lactic acid, methoxyacetic acid using tetrahydrofuran, dimethyformamide, dichloromethane as solvents, in the same manner as described in Example 30-(2).

EXAMPLE 31

Compound 31 appearance: pale yellow oil

IR(neat, cm$^{-1}$): 1743,1638,1515,1464,1437,1344,1248, 1179,1122,1092,1032

High Resolution FAB-MS(m/z, $(C_{32}H_{40}N_2O_6+H)^+$): Calcd.: 549.2965. Found: 549.2985.

$^1$H-NMR(300 MHz, CDCl$_3$, δ ppm): 2.21+2.22+2.23+2.26(6H,s×4),2.20–3.60(11H,m), 3.74+3.75(3H,s×2),3.86+3.88(3H,s×2),3.92+3.94 (3H,s×2),4.20–4.40(1H,m),4.62–4.82+5.93–6.05 (1H,m×2),5.07+5.14(1H,d×2,J=11.2 Hz,J=11.2 Hz), 5.38+5.41(1H,d×2,J=11.2 Hz,J=11.2 Hz),6.41+6.46 (1H,s×2),6.65–6.85(4H,m),7.30–7.50(4H,m)

EXAMPLE 32

Compound 32 appearance: pale yellow oil

IR(neat, cm$^{-1}$): 1644,1515,1497,1458,1248,1122,1089, 1032

High Resolution FAB-MS(m/z, $(C_{32}H_{40}N_2O_6+H)^+$): Calcd.: 549.2965. Found: 549.2985.

$^1$H-NMR(300 MHz, CDCl$_3$, δ ppm): 0.43+0.96+1.01+1.26(3H,d×4,J=6.6 Hz,J=6.6 Hz, J=6.6 Hz,J=6.6 Hz),2.24+2.28+2.33(6H,s×3),2.50–3.10(4H,m),3.13–3.70(4H,m),3.74+3.86(3H,s×2), 3.86+3.87(3H,s×2),3.88+3.89+3.92(3H,s×3),4.96+- 5.03+5.08+5.12(1H,d×4,J=11.0 Hz,J=11.0 Hz, J=11.0 Hz,J=11.0 Hz),5.20+5.30+5.42+5.46(1H,d×4, J=11.0 Hz,J=11.0 Hz,J=11.0 Hz),4.75+4.88+5.88+5.99(1H,dd×4,J=10.9 Hz,3.0 Hz,J=9.1 Hz,2.4 Hz, J=7.9 Hz,5.5 Hz,J=9.7 Hz,4.2 Hz),4.28–4.45+4.61–4.72 (1H,m×2),6.41+6.43+6.47(1H,s×3),6.63–6.87(4H, m),7.30–7.60(4H,m)

EXAMPLE 33

Compound 33 appearance: yellow oil

IR(neat, cm$^{-1}$): 2938,2824,2776,1659,1611,1584,1518, 1500,1458,1368,1344,1305,1248,1179, 1122,1089,1032

High Resolution FAB-MS(m/z, (C$_{32}$H$_{40}$N$_2$O$_6$+H)$^+$): Calcd.: 549.2965. Found: 549.2986.

$^1$H-NMR(300 MHz, CDCl$_3$, δ ppm): 2.26+2.31(6H,s×2),2.50-3.10(4H,m),2.80(1H,d, J=14.2 Hz),3.02(3H,s),3.14-3.27(1H,m),3.35(1H,d, J=14.2 Hz),3.48(2H,s),3.73+3.74(3H,s×2),3.86+3.88(3H,s×2),3.87+3.93(3H,s×2),4.70-4.82(1H, m),4.70-4.82+5.95-6.02(1H,m×2),5.03+5.05(1H,d×2,J=10.7 Hz,J=10.7 Hz),5.22+5.39(1H,d×2,J=10.7 Hz, J=10.7 Hz),6.41+6.46(1H,s×2),6.65-6.88(4H,m), 7.30-7.52(4H,m)

EXAMPLE 34

(1) Preparation of 6,7-dimethoxy-8-(3-dimethylaminomethylbenzyloxy)-1-(3-methoxybenzyl)-1,2,3,4-tetrahydroisoquinoline The desired compound was prepared as a yellow oil (yield: 622 mg) using compound 7 obtained in Example 7 (772 mg, 1.53 mmole), in the same manner as described in Example 30-(1).

FAB-MS(m/z, (C$_{29}$H$_{36}$N$_2$O$_4$+H)$^+$): 477

(2) Preparation of Compound 34

The captioned compound was prepared as a colorless oil (yield: 42.2 mg) using the compound obtained in (1) (62.1 mg, 0.130 mmole), in the same manner as described in Example 30-(2).

IR(neat, cm$^{-1}$): 2944,1647,1605,1584,1497,1458,1344, 1266,1122,1083,1032

High Resolution FAB-MS(m/z, (C$_{31}$H$_{38}$N$_2$O$_4$+H)$^+$): Calcd.: 535.2808. Found: 535.2831.

$^1$H-NMR(300 MHz, CDCl$_3$, δ ppm): 2.23+2.27(6H,s×2),2.68-2.80(1H,m),2.80-3.00(1H, m),2.75(1H,d,J=14.5 Hz),2.78(1H,dd,J=10.5 Hz, 13.4 Hz),3.09(1H,dd,J=2.6 Hz,13.4 Hz),3.20-3.40(1H, m),3.40(1H,d,J=14.5 Hz),3.46+4.07(2H,s×2),3.65+3.69(3H,s×2),3.86+3.88(3H,s×2),3.86+3.93(3H,s×2),4.47+5.95(1H,dd×2,J=2.6 Hz,10.5 Hz,J=4.6 Hz, 8.1 Hz),4.65-4.76(1H,m),5.06+5.09(1H,d×2, J=11.2 Hz,J=10.9 Hz),5.19+5.39(1H,d×2,J=11.2 Hz, J=10.9 Hz),6.40-6.52(3H,m),6.70+6.71(1H,dd×2, J=1.9 Hz,8.1 Hz,J=1.9 Hz,8.1 Hz),7.05+7.07(1H,t×2, J=7.8 Hz,J=7.8 Hz),7.30-7.50(4H,m)

Compounds 35~37 (Examples 35~37) were prepared by the condensation of the compound obtained in Example 34-(1) with the corresponding carboxylic acids, 3-hydroxypropionic acid, methoxyacetic acid, N-acetylsarcosine, using dimethyformamide, dichloromethane, dimethyformamide as solvents, in the same manner as described in Example 30-(2).

EXAMPLE 35

Compound 35 appearance: pale yellow oil

IR(neat, cm$^{-1}$): 1638,1605,1497,1458,1437,1266,1122, 1092,1032

High Resolution FAB-MS(m/z, (C$_{32}$H$_{40}$N$_2$O$_6$+H)$^+$): Calcd.: 549.2965. Found: 549.2976.

$^1$H-NMR(300 MHz, CDCl$_3$, δ ppm): 2.22+2.30(6H,s×2),2.60-2.94(3H,m),3.06-3.26(2H, m),3.30-3.95(4H,m),3.43(2H,s),3.66+3.70(3H,s×2),3.8-5+3.88(3H,s×2),3.86+3.93(3H,s×2),4.70-4.82+6.05-(2H,m+dd,J=3.4 Hz,8.0 Hz),5.08+5.11(1H, d×2,J=11.2 Hz,J=11.2 Hz),5.38+5.39(1H,d×2, J=11.2 Hz,J=11.2 Hz),6.40-6.55(3H,m),6.69+6.71(1H, dd×2,J=2.0 Hz,7.7 Hz,J=2.0 Hz,7.7 Hz),7.05+7.07(1H, t×2,J=7.7 Hz,J=7.7 Hz),7.25-7.50(4H,m)

EXAMPLE 36

Compound 36 appearance: colorless oil

IR(neat, cm$^{-1}$): 2944,1656,1605,1497,1458,1440,1266, 1122,1089

High Resolution FAB-MS(m/z, (C$_{32}$H$_{40}$N$_2$O$_6$+H)$^+$): Calcd.: 549.2965. Found: 549.2979.

$^1$H-NMR(300 MHz, CDCl$_3$, δ ppm): 2.25+2.29(6H,s×2),2.50-2.65+2.65-2.77(1H,m×2), 2.80(1H,dd,J=10.6 Hz,13.6 Hz),2.85(1H,d,J=14.3 Hz), 2.77-2.96(1H,m),3.01+3.20(3H,s×2),3.10(1H,dd, J=2.6 Hz,13.6 Hz),3.15-3.30(1H,m),3.36(1H,d, J=14.3 Hz),3.47+3.49(2H,s×2),3.66+3.68(3H,s×2), 3.85+3.88(3H,s×2),3.86+3.93(3H,s×2),4.70-4.82 (1H,m),4.80+6.05(1H,dd×2,J=2.6 Hz,10.6 Hz, J=3.5 Hz,8.9 Hz),5.05+5.08(1H,d×2,J=11.0 Hz, J=11.0 Hz),5.20+5.38(1H,d×2,J=11.0 Hz,J=11.0 Hz), 6.41+6.46(1H,s×2),6.45-6.58(2H,m),6.66+6.71(1H, dd×2,J=1.8 Hz,7.8 Hz,J=1.8 Hz,7.8 Hz),7.05+7.08(1H, t×2,J=7.8 Hz,J=7.8 Hz),7.31-7.55(4H,m)

EXAMPLE 37

Compound 37 appearance: colorless oil

IR(neat, cm$^{-1}$): 1662,1605,1497,1458,1437,1269,1122, 1089,1032

High Resolution FAB-MS(m/z, (C$_{34}$H$_{43}$N$_3$O$_6$+H)$^+$): Calcd.: 590.3230. Found: 590.3190.

$^1$H-NMR(300 MHz, CDCl$_3$, δ ppm): 1.47+2.02+2.09(3H,s×3),2.09(1H,d,J=16.1 Hz), 2.20+2.25+2.29(6H,s×3),2.47+2.48+2.79(3H,s×3), 2.60-2.97(2H,m),3.05-3.30(2H,m),3.38-3.75(3H,m), 3.66+3.70+3.73(3H,s×3),3.84+3.88+3.89(3H,s×3), 3.85+3.92+3.94(3H,s×3),4.28+4.37(1H,d×2, J=16.1 Hz,J=16.1 Hz),4.50-4.60.+4.70-4.82+6.03(2H, m×2+dd,J=3.5 Hz,7.6 Hz),5.06+5.14+5.26(1H,d×3, J=11.1 Hz,J=10.8 Hz,J=11.4 Hz),5.15+5.38+5.40(1H,d×3,J=11.1 Hz,J=10.8 Hz,J=11.4 Hz),6.40-6.60(3H,m), 6.63-6.75(1H,m),7.05+7.06+7.12(1H,t×3,J=8.0 Hz, J=8.0 Hz,J=8.0 Hz),7.27-7.52(4H,m)

EXAMPLE 38

Preparation of Compound 38

The compound obtained in Example 34-(1) (57.8 mg, 0.121 mmole) was dissolved in dichloromethane (1 ml), and triethylamine (26 μl, 0.187 mmole) and methanesulfonyl chloride (15 μl, 0.194 mmole) were added under an argon atmosphere at 0° C., and the mixture was stirred for 1 hour. The reaction mixture was diluted with ethyl acetate, washed successively with a saturated aqueous sodium hydrogencarbonate solution, brine, dried over MgSO$_4$ and concentrated under reduced pressure. The residue was purified by preparative thin-layer chromatography (Merck, silica gel 60F$_{254}$/chloroform: methanol=15:1) to give the captioned compound (50.6 mg) as a colorless oil.

IR(neat, cm$^{-1}$): 1602,1584,1497,1461,1320,1263,1146, 1122,1068,1029

High Resolution FAB-MS(m/z, (C$_{30}$H$_{38}$N$_2$O$_6$S+H)+): Calcd.: 555.2529. Found: 555.2533.

$^1$H-NMR(300 MHz, CDCl$_3$, δ ppm): 2.05(3H,s),2.26(6H,s),2.61(1H,ddd,J=1.6 Hz,4.2 Hz, 16.8 Hz),2.71(1H,dd,J=10.7 Hz,13.9 Hz),3.00(1H,ddd, J=6.4 Hz,11.7 Hz,16.8 Hz),3.19(1H, dd,J=3.7 Hz, 13.9 Hz),3.38–3.48(1H,m),3.49(2H,s),3.68(3H,s), 3.80–4.00(1H,m),3.86(3H,s),3.90(3H,s),5.08(1H,d, J=11.0 Hz),5.13(1H,dd,J=3.7 Hz,10.7 Hz),5.31(1H,d, J=11.0 Hz),6.43(1H,s),6.52(1H,d,J=7.8 Hz),6.55(1H, d,J=2.0 Hz),6.70(1H,dd,J=2.0 Hz,7.8 Hz),7.08(1H,t, J=7.8 Hz),7.32–7.44(2H,m),7.46–7.51(2H,m)

EXAMPLE 39

Preparation of Compound 39

The compound obtained in Example 34-(1) (57.5 mg, 0.121 mmole) was dissolved in chloroform (1 ml), and acetic anhydride (22 μl, 0.233 mmole) was added under an argon atmosphere at 0° C., and the mixture was stirred overnight at room temperature. The reaction mixture was diluted with ethyl acetate, washed successively with a saturated aqueous sodium hydrogencarbonate solution, brine, dried over MgSO$_4$. The solvent was evaporated, and the residue was purified by preparative thin-layer chromatography (Merck, silica gel 60F$_{254}$/chloroform: methanol=10:1) to give the captioned compound (57.4 mg) as a colorless oil.

IR(neat, cm$^{-1}$): 1647,1605,1497,1458,1428,1266,1122, 1101,1029

High Resolution FAB-MS(m/z, (C$_{31}$H$_{38}$N$_2$O$_5$+H)+): Calcd.: 519.2859. Found: 519.2835.

$^1$H-NMR(300 MHz, CDCl$_3$, δ ppm): 1.22+2.02(3H,s×2),2.22+2.31(6H,s×2),2.40–2.60+2.-60–2.74(1H,m×2),2.79(1H,dd,J=10.5 Hz,13.4 Hz), 2.75–2.95(1H,m),3.11(1H,dd,J=2.6 Hz,13.4 Hz),3.07–3.26(1H,m),3.43(2H,s),3.65+3.69(3H,s×2), 3.26(1H,m),3.43(2H,s),3.65+3.69(3H,s×2), 3.85+3.88(3H,s×2),3.85+3.93(3H,s×2),4.70–4.80 (1H,m),4.80+6.07(1H,dd×2,J=2.6 Hz,10.5 Hz, J=4.6 Hz,8.7 Hz),5.02+5.12(1H,d×2,J=10.9 Hz, J=10.9 Hz),5.17+5.38(1H,d×2,J=10.9 Hz,J=10.9 Hz), 6.41+6.46(1H,s×2),6.45–6.55(2H,m),6.68+6.71(1H, dd×2,J=2.1 Hz,7.8 Hz,J=2.1 Hz,7.8 Hz),7.04+7.07(1H, t×2,J=7.8 Hz,J=7.8 Hz),7.28–7.50(4H,m)

EXAMPLE 40

Preparation of Compound 40

The compound obtained in Example 30-(1) (54.7 mg, 0.115 mmole) was dissolved in tetrahydrofuran (1.5 ml), and methyl isocyanate (12 μl, 0.203 mmole) was added under an argon atmosphere at 0° C. The mixture was stirred at 0° C. for 1 hour and at room temperature for 2 hours. The reaction mixture was concentrated under reduced pressure, and the residue was purified by preparative thin-layer chromatography (Merck, silica gel F$_{254}$/chloroform:methanol=10:1) to give the captioned compound (59.2 mg) as pale yellow amorphous.

IR(KBr, cm$^{-1}$): 2944,1632,1518,1497,1467,1425,1344, 1248,1122,1086,1032

High Resolution FAB-MS(m/z, (C$_{31}$H$_{39}$N$_3$O$_5$+H)+): Calcd.: 534.2968. Found: 534.2981.

$^1$H-NMR(300 MHz, CDCl$_3$, δ ppm): 2.23(6H,s),2.31(3H,d,J=4.6 Hz),2.58(1H,td, J=3.7 Hz,14.9 Hz),2.70(1H,dd,J=10.6 Hz,13.4 Hz), 2.78–2.92(1H,m),3.04–3.13(1H,m),3.07(1H, dd, J=3.0 Hz,13.4 Hz),3.13–3.30(1H,m),3.41(1H,d, J=12.8 Hz),3.47(1H,dJ=12.8 Hz),3.75(3H,s),3.87(3H, s),3.91(3H,s),4.29–4.40(1H,m),4.48–4.60(1H,m), 5.05(1H,d,J=11.3 Hz),5.34(1H,d,J=11.3 Hz),6.44(1H, s),6.69(2H,d,J=8.8 Hz),6.78(2H,d,J=8.8 Hz),7.30–7.45(4H,m)

EXAMPLE 41

Preparation of Compound 41

The captioned compound was prepared as pale yellow crystals (yield: 57.8 mg) using the compound obtained in Example 30-(1) (52.0 mg, 0.109 mmole) and methyl isothiocyanate (8.7 mg, 0.12 mmole), in the same manner described in Example 40.

IR(KBr, cm$^{-1}$): 3406,2938,2830,2776,1611,1584,1518, 1497,1467,1374,1344,1305,1245,1179, 1122,1086,1032,960,843,819,792

High Resolution FAB-MS(m/z, (C$_{31}$H$_{39}$N$_3$O$_4$S+H)+): Calcd.: 550.2739. Found: 550.2742.

$^1$H-NMR(300 MHz, CDCl$_3$, δ ppm): 2.26(6H,s),2.65(3H,d,J=4.1 Hz),2.81(1H,dd, J=10.0 Hz,13.4 Hz),2.95–3.10(1H,m),3.17(1H,dd, J=2.9 Hz,13.4 Hz),3.40–3.58(3H,m),3.74(3H,s),3.87 (3H,s),3.90(3H,s),4.22–4.35(1H,m),4.86–5.17(2H, m),5.02(1H,d,J=11.1 Hz),5.31(1H,d,J=11.1 Hz),6.45 (1H,s),6.68(2H,d,J=8.6 Hz),6.75(2H,d,J=8.6 Hz), 7.30–7.50(4H,m)

EXAMPLE 42

Preparation of Compound 42

2-(tert-Butyldimethylsiloxy)ethylamine (20.0 mg, 0.114 mmole) was dissolved in tetrahydrofuran (1 ml), and 1,1'-carbonyldiimidazole (18.5 mg, 0.114 mmole) was added at room temperature under an argon atmosphere, and the mixture was stirred for 30 minutes. To the mixture was added a solution of the compound obtained in Example 30-(1) (30.0 mg, 0.0629 mmole) in tetrahydrofuran (1 ml), and the mixture was stirred at room temperature for 6 hours. The reaction mixture was diluted with ethyl acetate, washed successively with water and brine. The organic layer was dried over MgSO$_4$ and concentrated under reduced pressure. The residue was purified by dry column flash chromatography (silica gel/chloroform: methanol=20:1) to give a pale yellow oil (32.5 mg). This product was dissolved in tetrahydrofuran (2 ml), and a 1.0M solution of tetrabutylammonium fluoride in tetrahydrofuran (60 μl) was added at 0° C., and the mixture was stirred for 2 hours. The reaction mixture was diluted with ethyl acetate, washed successively with water and brine, and dried over MgSO$_4$. The solvent was evaporated, and the residue was purified by preparative thin-layer chromatography (Merck, silica gel 60F$_{254}$/chloroform:methanol=8:1) to give the captioned compound (20.9 mg) as a colorless oil.

IR(neat, cm$^{-1}$): 3382,2944,2782,1614,1518,1467,1248, 1122,1086,1032,753

High Resolution FAB-MS(m/z, (C$_{32}$H$_{41}$N$_3$O$_6$+H)$^+$): Calcd.: 564.3074. Found: 564.3055.

$^1$H-NMR(300 MHz, CDCl$_3$, δ ppm): 2.24(6H,s),2.55-2.67(1H,m),2.72(1H,dd,J=10.4 Hz, 13.7 Hz),2.74-2.96(3H,m),3.08(1H,dd,J=2.7 Hz, 13.7 Hz),3.23(1H,ddd,J=4.5 Hz,11.5 Hz,13.3 Hz),3.33 (2H,t,J=5.1 Hz),3.44(1H,d,J=12.7 Hz),3.53(1H,d, J=12.7 Hz),3.68-3.74(2H,m),3.75(3H,s),3.87(3H,s), 3.94(3H,s),4.30-4.42(1H,m),4.46-4.58(1H,m),5.00 (1H,d,J=10.9 Hz),5.36(1H,d,J=10.9 Hz),6.46(1H,s), 6.70(2H,d,J=8.5 Hz),6.80(2H,d,J=8.5 Hz),7.31-7.55 (4H,m)

EXAMPLE 43

Preparation of Compound 43

To a solution of the compound obtained in Example 30-(1) (50.3 mg, 0.106 mmole) in dichloromethane (2 ml), were added 4-dimethylaminopyridine (8.0 mg, 0.065 mmole) and dimethylcarbamoyl chloride (15 μl, 0.163 mmole) at 0° C. under an argon atmosphere, and the mixture was stirred at room temperature for 6 hours. The reaction mixture was concentrated under reduced pressure, and the residue was purified by dry column flash chromatography (silica gel/chloroform:methanol=30:1) to give the captioned compound (47.8 mg) as a pale yellow oil.

IR(neat, cm$^{-1}$): 1644,1515,1497,1461,1248,1122,1095, 1032

High Resolution FAB-MS(m/z, (C$_{32}$H$_{41}$N$_3$O$_5$+H)$^+$): Calcd.: 548.3124. Found: 548.3094.

$^1$H-NMR(300 MHz, CDCl$_3$, δ ppm): 2.25(6H,s),2.41(6H,s),2.58-2.69(1H,m),2.80(1H, dd,J=10.7 Hz,14.2 Hz),2.80-3.00(1H,m),3.06(1H,dd, J=3.2 Hz,14.2 Hz),3.48-3.52(1H,m),3.47(2H,s),3.-75-3.88(1H,m),3.75(3H,s),3.85(3H,s),3.90(3H,s),5.06 (1H,d,J=10.9 Hz),5.33(1H,d,J=10.9 Hz),5.16(1H,dd, J=3.2 Hz,10.7 Hz),6.43(1H,s),6.68(2H,d,J=8.6 Hz), 6.89(2H,d,J=8.6 Hz),7.30-7.53(4H,m)

EXAMPLE 44

Preparation of Compound 44

The compound obtained in Example 30-(1) (29.8 mg, 0.0625 mmole) was dissolved in acetonitrile (2 ml), and chlorosulfonyl isocyanate (12 μl, 0.139 mmole) was added under nitrogen at 0° C., and the mixture was stirred at room temperature for 3 hours. To the mixture was added water (0.2 ml), and the reaction mixture was stirred for 1 hour. The resulting mixture was diluted with ethyl acetate, washed successively with a saturated aqueous sodium hydrogencarbonate solution and brine, and dried over MgSO$_4$. The organic layer was concentrated under reduced pressure and the residue was purified by preparative thin-layer chromatography (Merck, silica gel 60F$_{254}$/chloroform:methanol=7:1) to give the captioned compound (5.5 mg) as a pale yellow oil.

IR(neat, cm$^{-1}$): 1584,1515,1497,1467,1344,1248,1122, 1032,753

High Resolution FAB-MS(m/z, (C$_{30}$H$_{37}$N$_3$O$_5$+H)$^+$): Calcd.: 520.2812. Found: 520.2787.

$^1$H-NMR(300 MHz, CDCl$_3$, δ ppm): 2.32+2.61(6H,s×2),2.40-3.35(3H,m),2.72(1H,dd, J=10.0 Hz,13.7 Hz),3.09(1H,dd,J=3.0 Hz,13.7 Hz),3.59 (2H,s),3.75+3.84(3H,s×2),3.86+3.87(3H,s×2), 3.91+3.95(3H,s×2),4.25-4.45(1H,m),4.60-4.72(1H, m),5.03+5.06(1H,d×2,J=11.2 Hz,J=11.2 Hz),5.36+5.45(1H,d×2,J=11.2 Hz,J=11.2 Hz),6.38+6.44(1H,s×2),6.67(2H,d,J=8.8 Hz),6.77(2H,d,J=8.8 Hz),7.35-7.60(4H,m)

Compounds 45 and 46 (Examples 45 and 46) were prepared using compound 26 obtained in Example 26, in the same manner as described in Example 30-(1) and Examples 40,30-(2).

EXAMPLE 45

Compound 45 appearance: pale yellow amorphous

IR(KBr, cm$^{-1}$): 1638,1605,1539,1497,1461,1260,1122

High Resolution FAB-MS(m/z, (C$_{31}$H$_{39}$N$_3$O$_5$+H)$^+$): Calcd.: 534.2968. Found: 534.2996.

$^1$H-NMR(300 MHz, CDCl$_3$, δ ppm): 2.18(6H,s),2.32(3H,d,J=4.6 Hz),2.59(1H,td, J=3.3 Hz,16.2 Hz),2.76(1H,dd,J=10.0 Hz,13.3 Hz),2.87 (1H,td,J=5.3 Hz,16.2 Hz),3.10(1H,dd,J=3.0 Hz, 13.3 Hz),3.23(1H,ddd,J=3.3 Hz,5.3 Hz,13.2 Hz),3.14-3.19(1H,m),3.43(1H,d,J=12.9 Hz),3.56(1H,d, J=12.9 Hz),3.65(3H,s),3.87(3H,s),3.90(3H,s),4.24-4.35(1H,m),-4.59-4.69(1H,m),5.17(1H,d,J=11.7 Hz), 5.55(1H,d,J=11.7 Hz),6.36(1H,d,J=7.8 Hz),6.45(1H, s),6.47(1H,d,J=2.0 Hz),6.68(1H,dd,J=2.0 Hz,7.8 Hz), 7.04(1H,t,J=7.8 Hz),7.30-7.42(3H,m),7.55-7.62(1H, m)

EXAMPLE 46

Compound 46 appearance: colorless oil

IR(neat, cm$^{-1}$): 1650,1605,1497,1458,1266,1122,1083, 756

High Resolution FAB-MS(m/z, (C$_{31}$H$_{38}$N$_2$O$_6$+H)$^+$): Calcd.: 535.2808. Found: 535.2803.

$^1$H-NMR(300 MHz, CDCl$_3$, δ ppm): 2.21+2.24(6H,s×2),2.70-3.02(3H,m),2.77(1H,d, J=14.8 Hz),3.09(1H,dd,J=3.0 Hz,13.7 Hz),3.17-3.37 (1H,m),3.35-3.60(2H,m),3.52(1H,d,J=14.8 Hz),3.64 (3H,s),3.84+3.88(3H,s×2),3.89+3.92(3H,s×2), 4.45+5.90(1H,dd×2,J=3.0 Hz,10.5 Hz,J=4.8 Hz, 7.2 Hz),4.65-4.76(1H,m),5.14+5.21(1H,d×2, J=11.7 Hz,J=11.7 Hz),5.39+5.62(1H,d×2,J=11.7 Hz, J=11.7 Hz),6.34(1H,d,J=7.6 Hz),6.41(1H,d,J=2.0 Hz), 6.47(1H,s),6.69+6.70(1H,dd×2,J=2.0 Hz,7.6 Hz, J=2.0 Hz,7.6 Hz),7.03+7.05(1H,t×2,J=7.6 Hz, J=7.6 Hz),7.30-7.66(4H,m)

EXAMPLE 47

(1) Preparation of 2-chloroacetyl-6,7-dimethoxy-8-(3-dimethylaminomethylbenzyloxy)-1-(4-methoxybenzyl)-1,2,3,4-tetrahydroisoquinoline The compound obtained in Example 30-(1) (210 mg, 0.440 mmole) was dissolved in dichloromethane (3 ml), and a solution of chloroacetic acid (92 mg, 0.538 mole) in dichloromethane (0.5 ml) was added at room temperature under an argon atmosphere, and the mixture was stirred for 30 minutes. The reaction mixture was diluted with ethyl acetate, washed successively with a saturated aqueous sodium hydrogencarbonate solution and brine. The organic layer was dried over MgSO$_4$ and concentrated under reduced pressure to give the desired compound (206 mg) as a pale yellow oil.

FAB-MS(m/z, (C$_{31}$H$_{37}$N$_2$O$_5$Cl+H)$^+$): 553

(2) Preparation of Compound 47

The compound obtained in (1) (100 mg, 0.187 mmole) was dissolved in dimethylformamide, and thioacetic S-acid (20 μl, 0.280 mole) was added at room temperature under an argon atmosphere, and the mixture was stirred for 6 hours. The reaction mixture was concentrated under reduced pressure, and the residue was purified by preparative thin-layer chromatography (Merck, silica gel 60F$_{254}$/chloroform:methanol=10:1) to give the captioned compound (50.1 mg) as a colorless oil.

IR(neat, cm$^{-1}$): 2944,2820,1695,1647,1515,1431,1248, 1122,1089,1032,960,835

High Resolution FAB-MS(m/z, (C$_{33}$H$_{40}$N$_2$O$_6$S+H)$^+$): Calcd.: 593.2686. Found: 593.2710.

$^1$H-NMR(300 MHz, CDCl$_3$, δ ppm): 2.24+2.26(6H,s×2),2.30+2.35(3H,s×2),2.34(1H,d, J=15.4 Hz),2.65-2.97(2H,m),2.74(1H,dd,J=10.6 Hz, 13.6 Hz),3.12(1H,dd,J=2.2 Hz,13.6 Hz),3.13-3.27(1H, m),3.28(1H,d,J=15.4 Hz),3.49+3.56(2H,s×2),3.75+3.76(3H,s×2),3.86+3.-88(3H,s×2),3.94(3H,s), 4.70-4.80(1H,m),4.91+5.95(1H,dd×2,J=2.2 Hz, 10.6 Hz,J=4.7 Hz,8.6 Hz),5.02+5.09(1H,d×2, J=10.9 Hz,J=10.7 Hz),5.16+5.43(1H,d×2,J=10.9 Hz, J=10.7 Hz),6.41+6.46(1H,s×2),6.63-6.85(4H,m), 7.34-7.57(4H,m)

EXAMPLE 48

Preparation of Compound 48

The compound obtained in Example 47-(1) (43.0 mg, 0.077 mmole) was dissolved in dimethyl sulfoxide (0.5 ml), and a 15% aqueous sodium methyl sulfide solution (55 μl) was added at room temperature under an argon atmosphere, and the mixture was stirred overnight. The reaction mixture was diluted with water and extracted with ethyl acetate. The combined organic layers were dried over MgSO$_4$, and concentrated under reduced pressure. The residue was purified by preparative thin-layer chromatography ( Merck, silica gel 60F$_{254}$/chloroform:methanol=10:1) to give the captioned compound (18.2 mg) as a pale yellow oil.

High Resolution FAB-MS (m/z, (C$_{32}$H$_{40}$N$_2$O$_5$S+H)$^+$): Calcd.: 565.2736. Found: 565.2746.

$^1$H-NMR(300 MHz, CDCl$_3$, δ ppm): 1.92(3H,s),2.29+2.33(6H,s×2),2.61(2H,s),2.73 (1H,dd,J=10.3 Hz,13.4 Hz),2.80-2.95(1H,m),3.09(1H, dd,J=2.8 Hz,13.6 Hz),3.12-3.24(1H,m),3.53(2H,s), 3.55-3.68(1H,m),3.73+3.75(3H,s×2),3.87+3.88(3H, s×2),3.93+3.95(3H,s×2),4.90+5.95-6.02(1H,dd+m, J=2.0 Hz,10.3 Hz),4.72-4.81(1H,m),4.98+5.06(1H,d×2,J=10.8 Hz,J=10.8 Hz),5.22+5.45(1H,d×2,J=10.8 Hz, J=10.8 Hz),6.42+6.47(1H,s×2),6.63-6.73+6.83-6.90 (4H,m×2),7.38-7.55(4H,m)

EXAMPLE 49

Preparation of Compound 49

The compound obtained in Example 47-(1) (70.5 mg, 0.127 mmole) was dissolved in ethanol, and morpholine (350 μl, 4.01 mmole) was added under an argon atmosphere, and the mixture was heated under reflux for 3 hours. The reaction mixture was concentrated under reduced pressure, and ethyl acetate was added to the residue. The mixture was washed with brine, dried over MgSO$_4$ and concentrated under reduced pressure. The residue was purified by preparative thin-layer chromatography (Merck, silica gel 60F$_{254}$/chloroform:methanol=10:1) to give the captioned compound (67.2 mg) as a colorless oil.

IR(neat, cm$^{-1}$): 1644,1515,1458,1344,1248,1119,1092, 1029 pp High Resolution FAB-MS(m/z, (C$_{35}$H$_{45}$N$_3$O$_6$+H)$^+$): Calcd.: 604.3387. Found: 604.3367.

$^1$H-NMR(300 MHz, CDCl$_3$, δ ppm): 2.05(1H,d,J=14.4 Hz),2.14(4H,t,J=4.6 Hz),2.26+2.31 (6H,s×2),2.44(1H,d,J=14.4 Hz),2.60-3.00(3H,m), 3.07(1H,dd,J=2.5 Hz,13.8 Hz),3.14-3.30(1H,m),3.-45-3.65(6H,m),3.72+3.75(3H,s×2),3.86+3.88(3H,s×-2),3.88+3.91(3H,s×2),4.76+6.06(1H,dd×2, J=5.9 Hz,11.9 Hz,J=3.5 Hz,10.0 Hz),5.06+5.20(1H,d×2,J=10.7 Hz,J=11.0 Hz),5.24+5.35(1H,d×2,J=10.7 Hz, J=11.0 Hz),5.10-5.20(1H,m),6.42+6.46(1H,s×2), 6.66+6.69(2H,d×2,J=8.8 Hz,J=8.8 Hz),6.76+6.87(2H, d×2,J=8.8 Hz,J=8.8 Hz),7.36-7.57(4H,m)

Compounds 50 and 51 (Examples 50 and 51) were prepared using the compound obtained in Example 34-(1), in the same manner as described in Examples 48 and 47. Compound 52 (Example 52) was prepared using intermediate 5 obtained in Referential Example 5, in the same manners as described in Examples 26,30-(1) and 47. Compound 53 (Example 53) was prepared using compound 20 obtained in Example 20, in the same manners as described in Examples 30-(1) and 47.

EXAMPLE 50

Compound 50 appearance: pale yellow oil

IR(neat, cm$^{-1}$): 1644,1605,1497,1458,1437,1266,1122, 1089

High Resolution FAB-MS(m/z, (C$_{32}$H$_{40}$N$_2$O$_5$S+H)$^+$): Calcd.: 565.2736. Found: 565.2765.

$^1$H-NMR(300 MHz, CDCl$_3$, δ ppm): 1.91(3H,s),2.26+2.28(6H,s×2),2.33(1H,d, J=14.1 Hz),2.41(1H,d,J=14.1 Hz),2.55-2.80(1H,m), 2.79(1H,dd,J=10.4 Hz,13.4 Hz),2.80-2.97(1H,m),3.15 (1H,dd,J=2.5 Hz,13.4 Hz),3.15-3.29(1H,m),3.50(2H, s),3.65+3.66(3H,s×2),3.86+3.88(3H,s×2),3.87+3.94(-3H,s×2),4.71-4.82(1H,m),4.99+6.06(1H,dd×2,J=2.5 Hz,10.4 Hz,J=4.1 Hz,8.8 Hz),5.03+5.08(1H,d×2,J=10.8 Hz,J=10.8 Hz),5.21+5.43(1H,d×2,J=10.8 Hz, J=10.8 Hz),6.48-6.60(3H,m),6.67+6.70(1H,dd×2, J=2.1 Hz,7.5 Hz,J=2.1 Hz,7.5 Hz),7.04+7.05(1H,t×2, J=7.5 Hz,J=7.5 Hz),7.35-7.55(4H,m)

EXAMPLE 51

Compound 51 appearance: brown oil
IR(neat, cm$^{-1}$): 1698,1650,1605,1497,1458,1437,1269, 1122,1089,1032
High Resolution FAB-MS(m/z, (C$_3$H$_{40}$N$_2$O$_6$S+H)$^+$): Calcd.: 593.2686. Found: 593.2690.
$^1$H-NMR(300 MHz, CDCl$_3$, δ ppm): 2.24+2.29(6H,s×2),2.24+2.35(3H,s×2),2.44(1H,d, J=15.4 Hz),2.65-2.77(1H,m),2.80(1H,dd,J=10.7 Hz, 13.4 Hz),2.75-2.95(1H,m),3.13-3.30(2H,m),3.28(1H, d,J=15.4 Hz),3.47+3.54(2H,s×2),3.65+3.68(3H,s×2),3.85+3.88(3H,s×2),3.86+3.93(3H,s×2),4.69-4.79(1H,m),4.95-5.03+6.01(1H,m+dd,J=5.8 Hz, 8.1 Hz),5.01+5.13(1H,d×2,J=10.9 Hz,J=10.9 Hz), 5.14+5.39(1H,d×2,J=10.9 Hz,J=10.9 Hz),6.40-6.55 (3H,m),6.68+6.71(1H,dd×2,J=2.3 Hz,7.8 Hz,J=2.3 Hz, 7.8 Hz),7.04+7.08(1H,t×2,J=7.8 Hz,J=7.8 Hz),7.30-7.50(4H,m)

EXAMPLE 52

Compound 52 appearance: colorless oil
IR(neat, cm$^{-1}$): 2944,2836,2770,1695,1647,1506,1464, 1344,1227,1122,1089,966,753
High Resolution FAB-MS(m/z, (C$_{34}$H$_{42}$N$_2$O$_7$S+H)$^+$): Calcd.: 623.2791. Found: 623.2783.
$^1$H-NMR(300 MHz, CDCl$_3$, δ ppm): 2.21+2.26(6H,s×2),2.25+2.33(3H,s×2),2.76-3.21 (4H,m),3.36-3.85(5H,m),3.53+3.55(3H,s×2),3.57+3.59(3H,S×2),3.80+3.85(3H,S×2),3.86+3.88(3H,s×2),4.47(1H,ddd,J=3.4 Hz,5.9 Hz,13.0 Hz),5.11+5.25 (1H,d×2,J=11.8 Hz,J=11.9 Hz),5.19+6.06(1H,dd×2, J=3.0 Hz,8.7 Hz,J=5.1 Hz,9.0 Hz),5.32+5.46(1H,d×2, J=11.8 Hz,J=11.9 Hz),6.33-6.52(1H,m),6.45+6.50(1H, s×2),6.60-6.70(2H,m),7.22-7.49(3H,m),7.63-7.74 (1H,m)

EXAMPLE 53

Compound 53 appearance: yellow oil
IR(neat, cm$^{-1}$): 2920,2812,1695,1647,1482,1440,1263, 1209,1116,1041,966,753
High Resolution FAB-MS(m/z, (C$_{34}$H$_{38}$N$_2$O$_7$S+H)$^+$): Calcd.: 619.2478. Found: 619.2474.
$^1$H-NMR(300 MHz, CDCl$_3$, δ ppm): 2.23+2.34(3H,s×2),2.33-2.49(4H,m),2.52(1H,d, J=15.4 Hz),2.61-2.95(3H,m),3.08-3.27(2H,m),3.38 (1H,d,J=15.4 Hz),3.50(2H,s),3.57-3.73(4H,m), 3.66+3.75( 3H,s×2 ), 4.63-4.74 (1H,m),5.03+5.95-6.05(1H,dd+m,J=2.2 Hz,10.3 Hz),5.22+5.35(1H,s+d, J=11.0 Hz ),5.22+5.44(1H,s+d,J=11.0 Hz),5.92+5.97 (1H, d+s,J=7.8 Hz),5.93+5.97(1H,d+s,J=7.8 Hz),6.31+6.37(1H,s×2),6.45-6.56(2H,m),6.64-6.77(1H,m), 7.00-7.12(1H,m),7.26-7.52(4H,m)

EXAMPLE 54

(1) Preparation of 2-chloroacetyl-6,7-dimethoxy-8-(2-dimethylaminomethylbenzyloxy)-1-(3-methoxybenzyl)-1,2,3,4-tetrahydroisoquinoline The desired compound was prepared as a pale yellow oil (yield: 83 mg) using compound 26 obtained in Example 26 (104 mg), in the same manner as described in Example 30-(1) and Example 47-(1).
FAB-MS(m/z, (C$_{31}$H$_{37}$N$_2$O$_5$Cl+H)$^+$): 553

(2) Preparation of Compound 54

To a suspension of sodium hydride (6.5 mg, 0.162 mmole,60%) in dimethylformamide (1 ml) was added 2-pyrrolidone (12 μl, 0.158 mole), and the mixture was stirred at 70° C. under an argon atmosphere for 10 minutes. The mixture was cooled to room temperature. To the mixture was added dropwise a solution of the compound obtained in (1) (83.0 mg, 0.150 mmole) in dimethylformamide (1 ml), and the reaction mixture was stirred at room temperature for 1 hour. Water was added to the mixture, and the mixture was extracted with ethyl acetate. The combined organic layers were washed with brine, dried over MgSO$_4$ and concentrated under reduced pressure. The residue was purified by preparative thin-layer chromatography (Merck, silica gel 60F$_{254}$/chloroform:methanol=10:1), and was triturated in ether to give the captioned compound (65.4 mg) as a colorless powder.
IR(KBr, cm$^{-1}$): 2944,1692,1659,1605,1497,1458,1269, 1122
High-Resolution FAB-MS(m/z, (C$_{35}$H$_{43}$N$_3$O$_6$+H)$^+$): Calcd.: 602.3230. Found: 602.3230.
$^1$H-NMR(300 MHz, CDCl$_3$, δ ppm): 1.80-2.05(2H,m),2.13(1H,d,J=16.3 Hz),2.22(6H,s), 2.20-2.40(2H,m),2.55(1H,dt,J=5.4 Hz,8.4 Hz),2.60-3.00(2H,m),2.81(1H,dd,J=10.7 Hz,13.2 Hz),3.13(1H, dd,J=2.6 Hz,13.2 Hz),3.15-3.30(2H,m),3.45-3.60(2H, m),3.62+3.65(3H,s×2),3.84+3.89(3H,s×2), 3.87+3.91(3H,s×2),4.02(1H,d,J=16.3 Hz),4.70-4.78+5.98(1H,m+dd,J=4.8 Hz,14.9 Hz),4.72-4.81(1H, m),5.12+5.31(1H,d×2,J=11.9 Hz,J=11.9 Hz), 5.39+5.59(1H,d×2,J=11.9 Hz,J=11.9 Hz),6.32(1H,d, J=7.6 Hz),6.35-6.55(1H,m),6.46(1H,s),6.65+6.71 (1H,dd×2,J=1.8 Hz,7.8 Hz,J=1.8 Hz,7.8 Hz),7.04(1H, t,J=7.8 Hz),7.25-7.45(3H,m),7.59-7.70(1H,m)

EXAMPLE 55

Preparation of Compound 55

To a suspension of 6,7-dimethoxy-1-(4-methoxybenzyl)-1,2,3,4-tetrahydroisoquinolin-8-ol (50.3 mg, 0.153 mmole) in dichloromethane (1.5 ml) were added triethylamine (25 μl, 0.18 mmole) and methyl chloroformate (14 μl, 0.18 mmole) at 0° C., and the reaction mixture was stirred at room temperature for 4 hours. The reaction mixture was diluted with dichloromethane, washed successively with 10% aqueous citric acid and brine. The organic layer was dried over MgSO$_4$ and concentrated under reduced pressure to give a yellow oil. Using this product, the captioned compound was prepared as a pale yellow oil (22.5 mg) in the same manner as described in Example 1-(1).

IR(neat, cm$^{-1}$): 2944,2770,1704,1608,1518,1458,1368, 1248,1119,1032,840,792,759

High Resolution FAB-MS (m/z, (C$_{31}$H$_{38}$N$_2$O$_6$+H)$^+$): Calcd.: 535.2808. Found: 535.2841.

$^1$H-NMR (300 MHz, CDCl$_3$, δ ppm): 9.24(6H,s),2.40–2.91(2H,m),2.69(1H,dd,J=10.3 Hz, 13.7 Hz),3.06(1H,dd,J=3.2 Hz,13.7 Hz),3.22+3.58(3H, s×2),3.28–3.42(1H,m),3.46(2H,s),3.74(3H,s),3.87 (3H,s),3.86+3.90(3H,s×2),4.20(1H,ddd,J=2.7 Hz, 6.2 Hz,8.7 Hz),5.04(1H,d,J=10.8 Hz),5.18+5.30(1H,d×2,J=10.8 Hz ,J=10.8 Hz),5.24+5.57(1H,dd×2, J=3.2 Hz,10.3 Hz,J=3.2 Hz,10.3 Hz),6.40+6.45(1H,s×2),6.68(2H,d,J=8.8 Hz),6.78+6.84(2H,d×2,J=8.8 Hz, J=8.8 Hz),7.30–7.50(4H,m)

Compounds 56 and 57 (Examples 56 and 57) were prepared using methanesulfonyl chloride, acetyl chloride in the same manner as described in Example 55.

EXAMPLE 56

Compound 56 appearance: pale yellow oil

High Resolution FAB-MS(m/z, (C$_{30}$H$_{38}$N$_2$O$_6$S+H)$^+$): Calcd.: 555.2529. Found: 555.2511.

$^1$H-NMR(300 MHz, CDCl$_3$, δ ppm): 2.04(3H,s),2.25(6H,s),2.57–2.68(1H,m),2.65(1H, dd,J=10.9 Hz,13.9 Hz),2.94–3.08(1H,m),3.13(1H,dd, J=3.4 Hz,13.9 Hz),3.38–3.45(1H,m),3.47(2H,s),3.75 (3H,s),3.84–3.89(1H,m),3.86(3H,s),3.91(3H,s), 5.02(1H,dd,J=3.4 Hz,10.9 Hz),5.04(1H,d,J=10.9 Hz), 5.32(1H,d,J=10.9 Hz),6.43(1H,s),6.67–6.72(2H,m), 6.79–6.83(2H,m),7.34–7.51(4H,m)

EXAMPLE 57

Compound 57 appearance: colorless oil

IR(neat, cm$^{-1}$): 2938,1650,1608,1518,1458,1428,1368, 1364,1248,1122,1098,1029,834,753

High Resolution FAB-MS(m/z, (C$_{31}$H$_{38}$N$_2$O$_5$+H)$^+$): Calcd.: 519.2859. Found: 519.2854.

$^1$H-NMR(300 MHz, CDCl$_3$, δ ppm): 1.19(3H,s),2.22+2.25(6H,s×2),2.62–2.92(2H,m), 2.73(1H,dd,J=10.7 Hz,13.7 Hz),3.06(1H,dd,J=2.7 Hz, 13.7 Hz),3.11–3.28(1H,m),3.42(2H,s),3.74+3.75(3H, s×2),3.85+3.88(3H,s×2),3.93(3H,s),4.72+5.96–6.05(1-H,dd+m,J=2.7 Hz,10.7 Hz),4.69–4.80(1H,m), 5.03+5.08(1H,d×2,J=11.1 Hz,J=11.1 Hz),5.16+5.40 (1H,d×2,J=11.1 Hz,J=11.1 Hz),6.40+6.45(1H,s×2), 6.65–6.83(4H,m),7.30–7.50(4H,m)

EXAMPLE 58

(1) Preparation of 6,7-dimethoxy-1-(4-methoxybenzyl)-2-(N,N-dimethylaminoacetyl)-1,2,3,4-tetrahydroisoquinolin-8-ol To a suspension of 6,7-dimethoxy-1-(4-methoxybenzyl)-1,2,3,4-tetrahydroisoquinolin-8-ol (103 mg, 0.312 mmole) in dichloromethane (2 ml) were added N,N-dimethylglysine hydrochloride (52.2 mg, 0.374 mole) and HOBt (57.3 mg, 0.374 mmole) at room temperature under nitrogen. Then triethylamine (56.5 μl, 0.405 mmole) and EDCI (71.7 mg, 0.374 mmole) were added to the mixture at 0° C. The reaction mixture was stirred at 0° C. for 1.5 hours and at room temperature for 5 hours. The reaction mixture was concentrated under reduced pressure, and water was added to the residue. The mixture was extracted with chloroform. The combined extracts were successively washed with a saturated aqueous sodium hydrogencarbonate solution and brine, dried over MgSO$_4$, and concentrated under reduced pressure. The residue was recrystallized from methanol to give the desired compound (78.4 mg) as colorless crystals.

m.p.: 185°–187° C.

FAB-MS(m/z, (C$_{23}$H$_{30}$N$_2$O$_5$+H)$^+$): 415

(2) Preparation of Compound 58

The captioned compound was prepared as a colorless oil (yield: 35.6 mg) using the compound obtained in (1) in the same manner as described in Example 1-(1).

IR(neat, cm$^{-1}$): 2938,2776,1611,1500,1344,1122,1035

High Resolution FAB-MS(m/z, (C$_{33}$H$_{43}$N$_3$O$_5$+H)$^+$): Calcd.: 562.3281. Found: 562.3257.

$^1$H-NMR(300 MHz, CDCl$_3$+D$_2$O, δ ppm): 1.96+2.08(6H,s×2),1.99(1H,d,J=14.4 Hz),2.25+2.26 (6H,s×2),2.40(1H,d,J=14.4 Hz),2.77(1H,dd, J=10.6 Hz,13.6 Hz),2.60–2.95(2H,m),3.10(1H,dd, J=2.6 Hz,13.6 Hz),3.06–3.25(1H,m),3.48+3.49(2H,s×2),3.72+3.75(3-H,s×2),3.86+3.88(3H,s×2),3.87+3.92(3H,s×2),4.67–4.75(1H,m),5.04(1H,d, J=10.9 Hz),5.22–5.26(1H,m),5.36(1H,d,J=10.9 Hz), 6.41+6.47(1H,s×2),6.66–6.73(2H,m),6.79–6.89(2H, m),7.33–7.49(4H,m)

Compounds 59 and 60 (Examples 59 and 60) were prepared by the reaction of 6,7-dimethoxy-1-(3-methoxybenzyl)-1,2,3,4-tetrahydroisoquinolin-8-ol with the corresponding chlorides, 3-chloromethyl-N,N-dimethylbenzylamine hydrochloride, N-(3-chloromethylbenzyl)-N'-methylpiperazine dihydrochloride, in the same manner as described in Example 55.

EXAMPLE 59

Compound 59 appearance: pale yellow oil

IR(neat, cm$^{-1}$): 2944,1704,1605,1497,1455,1341,1251, 1119,1032

High Resolution FAB-MS(m/z, (C$_{31}$H$_{38}$N$_2$O$_6$+H)$^+$): Calcd.: 535.2808. Found: 535.2834.

$^1$H-NMR(300 MHz, CDCl$_3$, δ ppm): 2.24(6H,s),2.40–2.53+2.63(1H,m+td,J=2.9 Hz, 14.6 Hz),2.76(1H,dd,J=10.3 Hz,13.5 Hz),2.75–2.92 (1H,m),3.11(1H,dd,J=3.2 Hz,13.5 Hz),3.24+3.60(3H,s×2),3.28–3.45(1H,m),3.45(2H,s),3.-66+3.67(3H,s×2),3.85+3.89(3H,s×2),3.87(3H,s),4.19-(1H,ddd, J=2.9 Hz,6.4 Hz,13.2 Hz),5.05+5.07(1H,d×2, J=11.0 Hz,J=11.0 Hz),5.17+5.28(1H,d×2,J=11.0 Hz, J=11.0 Hz),5.30+5.62(1H,dd×2,J=3.2 Hz,10.3 Hz, J=3.2 Hz,10.3 Hz),6.41+6.45(1H,s×2),6.45–6.60(2H, m),6.67(1H,dd,J=1.1 Hz,8.1 Hz),7.06(1H,t,J=8.1 Hz), 7.25–7.50(4H,m)

EXAMPLE 60

Compound 60 appearance: colorless oil

IR(neat, cm$^{-1}$): 2944,2800,1704,1605,1497,1458,1341, 1248,1164,1119,1014

High Resolution FAB-MS (m/z, $(C_{34}H_{43}N_3O_6+H)^+$): Calcd.: 590.3230. Found: 590.3209.

$^1$H-NMR(300 MHz, CDCl$_3$, δ ppm): 2.28(3H,s),2.33–2.60(8H,m),2.50–2.70(1H,m),2.75 (1H,dd,J=10.1 Hz,13.4 Hz),2.75–2.91(1H,m),3.10(1H, dd,J=3.6 Hz,13.4 Hz),3.24+3.60(3H,s×2),3.25–3.46 (1H,m),3.53(2H,s),3.66+3.67(3H,s×2),3.85+3.90 (3H,s×2),3.87(3H,s),4.13–4.24(1H,m),5.04+5.07 (1H,d×2,J=11.1 Hz,J=11.1 Hz),5.15+5.26(1H,d×2, J=11.1 Hz,J=11.1 Hz),5.29+5.61(1H,dd×2,J=3.6 Hz, 10.1 Hz,J=4.7 Hz,8.2 Hz),6.42+6.45(1H,s×2),6.47–6.59(2H,m),6.68(1H,d,J-=8.2 Hz,),7.06(1H,t, J=8.2 Hz),7.30–7.50(4H,m)

EXAMPLE 61

(1) Preparation of 6,7-dimethoxy-1-(3-methoxybenzyl)-2-(N-methylcarbamoyl)-1,2,3,4-tetrahydroisoquinolin-8-ol To a solution of 6,7-dimethoxy-1-(3-methoxybenzyl)-1,2,3,4-tetrahydroisoquinolin-8-ol (350 mg, 1.06 mole) in dichloromethane (11 ml) was added methyl isocyanate (69 μl, 1.17 mole) at room temperature under an argon atmosphere, and the reaction mixture was stirred for 3.5 hours. The reaction mixture was concentrated under reduced pressure, and the residue was purified by column chromatography (silica gel/chloroform:methanol=20:1) to give the desired compound (410 mg) as a colorless powder.

m.p.: 75°–80° C.

FAB-MS(m/z, $(C_{21}H_{26}N_2O_5+H)^+$): 387

(2) Preparation of Compound 61

The captioned compound was prepared as a yellow oil (yield: 58.1 mg) using the compound obtained in (1) (57.2 mg, 0.148 mmole) and 2-chloromethylpyridine hydrochloride (32.0 mg, 0.195 mmole) in the same manner as described in Example 1-(1).

IR(neat, cm$^{-1}$): 3376,2938,1635,1608,1542,1497,1461, 1440,1374,1344,1260,1194,1152,1122, 1086,1044,1005,759

High Resolution FAB-MS(m/z, $(C_{27}H_{31}N_3O_5+H)^+$): Calcd.: 478.2342. Found: 478.2359.

$^1$H-NMR(300 MHz, CDCl$_3$, δ ppm): 2.44(3H,d,J=4.7 Hz),2.56–2.68(1H,m),2.70–2.92(2H, m),3.10(1H,dd,J=3.2 Hz,13.4 Hz),3.24–3.36(1H,m), 3.69(3H,s),3.86(3H,s),3.90(3H,s),4.03–4.10(1H, m),4.29–4.37(1H,m),5.10–5.18(1H,m),5.11(1H,d, J=12.0 Hz),5.41(1H,d,J=12.0 Hz),6.46(1H,s),6.52–6.60(2H,m),6.-68–6.71(1H,m),7.08(1H,t,J=7.8 Hz), 7.25–7.31(1H,m),7.53(1H,d,J=8.5 Hz),7.76(1H,t, J=8.5 Hz),8.55–8.60(1H,m)

Compounds 62 and 63 (Examples 62 and 63) were prepared using 3-chloromethylpyridine hydrochloride, 4-chloromethylpyridine hydrochloride in the same manner as described in Example 61-(2). Compounds 64~67 (Examples 64~67) were prepared using the compound obtained in Example 61-(1), in the same manner as described in Example 22-(1) followed by the reaction with the corresponding amines, methylamine, piperazine, N-methylpiperazine, morpholine in the same manner as described in Example 22-(2).

EXAMPLE 62

Compound 62 appearance: yellow oil

IR(neat, cm$^{-1}$): 3376,2944,1635,1605,1584,1539,1497, 1470,1437,1374,1341,1263,1221,1152, 1122,1086,1029,756

High Resolution FAB-MS(m/z, $(C_{27}H_{31}N_3O_5+H)^+$): Calcd.: 478.2342. Found: 478.2365.

$^1$H-NMR(300 MHz, CDCl$_3$, δ ppm): 2.42(3H,d,J=4.9 Hz),2.75–2.92(1H,m),2.82(1H,dd, J=9.7 Hz,13.1 Hz),3.07(1H,dd,J=3.7 Hz,13.1 Hz),3.23–3.33(1H,m),3.-34–3.42(1H,m),3.69(3H,s),3.86(3H, s),3.87(3H,s),4.08–4.18(1H,m),4.76–4.84(1H,m), 5.12(1H,d,J=11.6 Hz),5.23(1H,d,J=11.6 Hz),6.47(1H, s),6.48–6.56(2H,m),6.68–6.74(1H,m),7.11(1H,t, J=8.1 Hz),7.33(1H,dd,J=4.9 Hz,7.6 Hz),7.77–7.82(1H, m),8.58–8.64(1H,m),8.71–8.77(1H,m)

EXAMPLE 63

Compound 63 appearance: pale yellow oil

High Resolution FAB-MS (m/z, $(C_{27}H_{31}N_3O_5+H)^+$): Calcd.: 478.2342. Found: 478.2320.

$^1$H-NMR(300 MHz, CDCl$_3$, δ ppm): 2.47(3H,d,J=4.6 Hz),2.50–2.70(1H,m),2.78–2.95(2H, m),3.08(1H,dd,J=4.1 Hz,12.2 Hz),3.29–3.42(1H,m), 3.49–3.60(1H,m),3.66(3H,s),3.78(3H,s),3.87(3H, s),3.94–4.10(1H,m),5.01(1H,dd,J=4.1 Hz,8.7 Hz), 5.11(2H,s),6.48(1H,s),6.50–6.70(2H,m),6.66–6.76 (1H,m),7.10(1H,t,J=7.7 Hz),7.41(2H,d,J=5.4 Hz), 8.12–8.30(2H,m)

EXAMPLE 64

Compound 64 appearance: pale yellow powder

IR(KBr, cm$^{-1}$): 2944,1608,1545,1497,1470,1260,1122, 753

High Resolution FAB-MS(m/z, $(C_{30}H_{37}N_3O_5+H)^+$): Calcd.: 520.2812. Found: 520.2804.

$^1$H-NMR(300 MHz, CDCl$_3$, δ ppm): 2.46(3H,s),2.58(3H,d,J=4.4 Hz),2.50–2.64(1H,m), 2.73(1H,dd,J=9.5 Hz,13.4 Hz),2.75–2.87(1H,m),2.98 (1H,dd,J=4.0 Hz,13.4 Hz),3.40–3.51(1H,m),3.52–3.70 (1H,m),3.68(3H,s),3.86(3H,s),3.92(3H,s),3.88(1H, d,J=12.1 Hz),4.11(1H,d,J=12.1 Hz),4.94(1H,d, J=11.8 Hz),5.41(1H,d,J=11.8 Hz),5.26–5.40(1H,m), 6.36(1H,d,J=7.7 Hz),6.40(1H,d,J=2.1 Hz),6.42(1H, s),6.68(1H,dd,J=2.1 Hz,7.7 Hz),7.07(1H,t,J=7.7 Hz), 7.35(1H,d,J=7.6 Hz),7.39(1H,t,J=7.6 Hz),7.58(1H,d, J=7.6 Hz),7.61(1H,s)

EXAMPLE 65

Compound 65 appearance: colorless powder

IR(KBr, cm$^-$): 1635,1605,1539,1497,1461,1341,1263, 1122,753

High Resolution FAB-MS(m/z, $(C_{33}H_{42}N_4O_5+H)^+$): Calcd.: 575.3234. Found: 575.3244.

$^1$H-NMR(300 MHz, CDCl$_3$, δ ppm): 2.33(3H,d,J=4.6 Hz),2.38–2.50(4H,m),2.56(1H,td, J=4.0 Hz,16.1 Hz),2.74(1H,dd,J=10.0 Hz,13.3 Hz), 2.75–2.90(1H,m),2.85–2.97(4H,m),3.11(1H,dd, J=2.8 Hz,13.3 Hz),3.16–3.30(1H,m),3.52(2H,s),3.69 (3H,s),3.87(3H,s),3.91(3H,s),4.15–4.25(1H,m), 4.63(1H,dd,J=2.8 Hz,10.0 Hz),5.13(1H,d,J=11.2 Hz), 5.29(1H,d,J=11.2 Hz),6.44(1H,s),6.46(1H,d, J=7.7 Hz),6.51(1H,d,J=2.4 Hz),6.70(1H,dd,J=2.4 Hz, 7.7 Hz),7.07(1H,t,J=7.7 Hz),7.25–7.45(4H,m)

EXAMPLE 66

Compound 66 appearance: pale yellow powder
IR(KBr, cm$^{-1}$): 1635,1605,1539,1497,1461,1344,1260, 1122
High Resolution FAB-MS(m/z, (C$_{34}$H$_{44}$N$_4$O$_5$+H)$^+$): Calcd.: 589.3390. Found: 589.3385.
$^1$H-NMR(300 MHz, CDCl$_3$, δ ppm): 2.30(3H,s),2.33(3H,d,J=4.6 Hz),2.35–2.60(8H,m), 2.57(1H,td,J=3.6 Hz,16.2 Hz),2.76(1H,dd,J=10.1 Hz, 13.3 Hz),2.79–2.92(1H,m),3.12(1H,dd,J=3.0 Hz, 13.3 Hz),3.15–3.30(1H,m),3.50(2H,s),3.69(3H,s), 3.87(3H,s),3.91(3H,s),4.23–4.33(1H,m),4.62(1H, dd,J=3.0 Hz,10.1 Hz),5.11(1H,d,J=11.1 Hz),5.29(1H, d,J=11.1 Hz),6.45(1H,s),6.48(1H,d,J=7.5 Hz),6.52 (1H,d,J=2.5 Hz),6.69(1H,dd,J=2.5 Hz,7.5 Hz),7.07 (1H,t,J=7.5 Hz),7.31–7.45(4H,m)

EXAMPLE 67

Compound 67 appearance: colorless powder
IR(KBr, cm$^{-1}$): 2944,1638,1605,1536,1497,1458,1341, 1266,1119
High Resolution FAB-MS(m/z, (C$_{33}$H$_{41}$N$_3$O$_6$+H)$^+$): Calcd.: 576.3074. Found: 576.3058.
$^1$H-NMR(300 MHz, CDCl$_3$, δ ppm): 2.33(3H,d,J=4.6 Hz),2.40(4H,t,J=4.6 Hz),2.57(1H, td,J=3.4 Hz,15.9 Hz),2.76(1H,dd,J=10.0 Hz,13.3 Hz), 2.75–2.90(1H,m),3.12(1H,dd,J=10.0 Hz,13.3 Hz), 3.15–3.30(1H,m),3.46(1H,d,J=13.4 Hz),3.50(1H,d, J=13.4 Hz),3.66(4H,t,J=4.6 Hz),3.69(3H,s),3.87(3H, s),3.90(3H,s),4.20–4.32(1H,m),4.62(1H,dd, J=2.8 Hz,10.0 Hz),5.12(1H,d,J=11.2 Hz),5.29(1H,d, J=11.2 Hz),6.45(1H,s),6.48(1H,d,J=7.6 Hz),6.53(1H, d,J=2.2 Hz),6.70(1H,dd,J=2.2 Hz,7.6 Hz),7.07(1H,t, J=7.6 Hz),7.30–7.48(4H,m)

EXAMPLE 68

Preparation of Compound 68

To a solution of compound 30 obtained in Example 30-(2) (25.4 mg, 0.0475 mmole) in dichloromethane (0.6 ml) were added 4-dimethylaminopyridine (5.8 mg, 0.047 mmole) and acetic anhydride (5.3 μl, 0.056 mmole), and the reaction mixture was stirred at room temperature for hours. The reaction mixture was concentrated under reduced pressure, and the residue was purified by preparative thin-layer chromatography (Merck, silica gel F$_{254}$/chloroform:methanol=10:1) to give the captioned compound (20.4 mg) as a colorless oil.
IR(neat, cm$^{-1}$): 2944,2820,2765,1755,1671,1614,1515, 1458,1371,1248,1122,1032,838,785
High Resolution FAB-MS(m/z, (C$_{33}$H$_{40}$N$_2$O$_7$+H)$^+$): Calcd.: 577.2914. Found: 577.2945.
$^1$H-NMR(300 MHz, CDCl$_3$, δ ppm): 2.03+2.16(3H,s×2),2.24+2.29(6H,s×2),2.64–2.96 (2H,m),2.74(1H,dd,J=10.8 Hz,13.7 Hz),3.02(1H,d, J=14.4 Hz),3.07(1H,dd,J=2.0 Hz,13.7 Hz),3.20(1H,dt, J=4.5 Hz,12.5 Hz),3.46+3.55(2H,s×2),3.74+3.76(3H, s×2),3.85+3.88(3H,s×2),3.86+3.93(3H,s×2),4.17 (1H,d,J=14.4 Hz),4.55+5.90(1H,dd×2,J=2.0 Hz, 10.5 Hz,J=5.5 Hz,7.3 Hz),4.67–4.77(1H,m),5.03+5.09 (1H,d×2,J=11.0 Hz,J=11.0 Hz),5.41(1H,d,J=11.0 Hz), 6.39+6.45(1H,s×2),6.64–6.82(4H,m),7.-31–7.50(4H, m)

EXAMPLE 69

Preparation of Compound 69

The captioned compound was prepared as a colorless oil (yield: 21.8 mg) using compound 30 obtained in Example 30-(2) (55.4 mg, 0.104 mmole), in the same manner as described in Example 30-(2).
IR(neat, cm$^{-1}$): 3412,2944,2836,1755,1645,1611,1515, 1457,1240,1179,1122,1080,1032,753
High Resolution FAB-MS(m/z, (C$_{33}$H$_{40}$N$_2$O$_8$+H)$^+$): 593
$^1$H-NMR(300 MHz, CDCl$_3$, δ ppm): 2.24+2.29(6H,s×2),2.43–2.95(3H,m),2.74(1H,dd, J=10.5 Hz,13.9 Hz),3.06(1H,dd,J=2.3 Hz,13.9 Hz), 3.11–3.29(1H,m),3.16(1H,d,J=14.2 Hz),3.47(2H,s), 3.76+3.77(3H,s×2),3.86+3.88(3H,s×2),3.93+3.94 (3H,s×2),4.08(1H,d,J=14.2 Hz),4.07–4.35(2H,m), 4.50+5.83(1H,dd×2,J=2.3 Hz,10.5 Hz,J=5.7 Hz, 7.8 Hz),4.60–4.71(1H,m),5.14+5.16(1H,d×2, J=11.2 Hz,J=11.2 Hz),5.39+5.40(1H,d×2,J=11.2 Hz, J=11.2 Hz),6.39+6.46(1H,s×2),6.63–6.71(4H,m), 7.29–7.48(4H,m)

EXAMPLE 70

Preparation of Compound 70

To a solution of compound 47 obtained in Example 47-(2) (19.5 mg, 0.0329 mmole) in methanol (0.5 ml) was added an aqueous potassium hydroxide solution (1N, 65° μl) under an argon atmosphere, and the mixture was stirred at room temperature for 4 hours. The reaction mixture was concentrated under reduced pressure, and the residue was purified by preparative thin-layer chromatography (Merck, silica gel 60F$_{254}$/chloroform:methanol=10:1) to give the captioned compound (14.5 mg) as a colorless oil.
IR(neat, cm$^{-1}$): 2938,2820,1644,1515,1458,1434, 1248,1122,1089,1032,753
High Resolution FAB-MS(m/z, (C$_{31}$H$_{38}$N$_2$O$_5$S+H)$^+$): Calcd.: 551.2579. Found: 551.2584.
$^1$H-NMR(300 MHz, CDCl$_3$, δ ppm): 2.27+2.30(6H,s×2),2.28–2.57(2H,m),2.59–2.98(3H, m),3.01–3.39(3H,m),3.42–3.63(2H,m),3.69+3.72(3H, s×2),3.76+3.86(3H,s×2),3.89+3.95(3H,s×2),4.57–4.- 71(1H,m),4.71–4.86+5.96–5.97(1H,m×2),4.- 93–5.11(1H,m),5.33–5.51(1H,m),6.39+6.47(1H,s×2), 6.56–6.87(4H,m),7.33–7.58(4H,m)

EXAMPLE 71

Preparation of Compound 71

The captioned compound was prepared as a yellow oil (yield: 48.3 mg) using intermediate 2 obtained in Referential Example 2 (90.0 mg, 0.252 mmole) and 3-nitrobenzyl chloride (56.1 mg, 0.327 mmole) in the same manner as described in Example 1-(1).
FAB-MS(m/z, (C$_{27}$H$_{28}$N$_2$O$_7$+H)$^+$): 493

1H-NMR(300 MHz, CDCl3, δ ppm): 2.60–3.00(2H,m),3.09(1H,dd,J=2.7 Hz,13.7 Hz),3.14–3.28 (1H,m),3.45–3.53(1H,m),3.69(3H,s),3.88(3H, s),3.89(3H,s),4.43(1H,ddd,J=2.5 Hz,6.3 Hz,12.6 Hz), 4.55+5.71–5.77(1H,dd+m,J=2.7 Hz,10.5 Hz),5.19+5.25 (1H,d×2,J=12.0 Hz,12.0 Hz),5.39(1H,d,J=12.0 Hz), 6.39+6.44(1H,s×2),6.47–6.60(2H,m),6.69–6.80(1H, m),7.08+7.12(1H,t×2,J=7.7 Hz,7.7 Hz),7.43+8.00 (1H,s×2),7.58+7.60(1H,t×2,J=7.8 Hz,7.8 Hz),7.78–7.88(1H,m),8.19–8.30(1H,m),8.36–8.42(1H,m)

EXAMPLE 72

Preparation of Compound 72

To a solution of Compound 71 obtained in Example 71 (48.0 mg, 0.0975 mole) in ethanol (2 ml) was added tin(II) chloride (93.2 mg, 0.492 mole) under nitrogen, and the reaction mixture was stirred at 70° C. for 1 hour. To the mixture was added an aqueous sodium hydrogen-carbonate solution, and the mixture was extracted with chloroform. The combined extracts were dried over MgSO4, and concentrated under reduced pressure. The residue was purified by preparative thin-layer chromatography (Merck, silica gel 60F254/chloroform:methanol=20:1) to give the captioned compound (29.2 mg) as a yellow oil.

IR(neat, cm$^{-1}$): 3370,2938,1668,1605,1497,1458,1437, 1374,1344,1296,1266,1236,1188,1155, 1122,1083,1032,1005,963,861,753,699

High Resolution FAB-MS (m/z, (C27H30N2O5+H)+): Calcd.: 463.2233. Found: 463.2270.

1H-NMR(300 MHz, CDCl3, δ ppm): 2.71(1H,dd,J=11.0 Hz,13.6 Hz),2.62–2.92(2H,m),3.15 (1H,dd,J=2.4 Hz,13.6 Hz),3.10–3.21(1H,m),3.69+3.73 (3H,s×2),3.85+3.88(3H,s×2),3.89+3.93(3H,s×2), 4.33–4.42+5.85–5.90(2H,m×2),5.01+5.02(1H,d×2, J=11.0 Hz,J=11.0 Hz),5.23+5.24(1H,d×2,J=11.0 Hz, J=11.0 Hz),6.39+6.46(1H,s×2),6.51–6.60(2H,m), 6.62–6.68(1H,m),6.69–6.80(3H,m),7.07–7.20(2H,m), 7.22+7.97(1H,s×2)

EXAMPLE 73

Preparation of Compound 73

To a solution of compound 2.4 (20.0 mg, 0.0355 mmole) in acetone (2 ml) was added an aqueous oxone solution (2 ml, 0.0223 mole), and the reaction mixture was stirred at room temperature for 15 hours. Water was added to the mixture, and the mixture was extracted with chloroform. The combined extracts were dried over MgSO4, and concentrated under reduced pressure. The residue was purified by preparative thin-layer chromatography (Merck, silica gel 60F254/chloroform:methanol=20:1) to give the captioned compound (14.3 mg) as a colorless oil.

IR(neat, cm$^{-1}$): 2938,2830,1671,1605,1584,1497,1458, 1437,1368,1344,1269,1236,1188,1155, 1122,1083,1056,1032,960,753,699

High Resolution FAB-MS(m/z, (C32H38N2O6S+H)+): Calcd.: 579.2529. Found: 579.2535.

1H-NMR(300 MHz, CDCl3, δ ppm): 2.56–3.32(13H,m),3.53(2H,s),3.67+3.71(3H,s×2), 3.86+3.88(3H,s×2),3.93(3H,s),4.29–4.42+5.-72–5.78(2H,m×2),5.12+5.16(1H,d×2,J=11.4 Hz, J=11.4 Hz),5.28+5.32(1H,d×2,J=11.4 Hz,J=11.4 Hz), 6.40–6.54(3H,m),6.- 66–6.73(1H,m),7.05+7.10(1H,t×2,J=7.9 Hz,J=7.9 Hz),7.19–7.53(4H,m),7.35–7.97(1H, s×2)

EXAMPLE 74

(1) Preparation of (1) optical isomer of Compound 1

The captioned compound was prepared as a colorless oil using (−)-6,7-dimethoxy-1-(4-methoxybenzyl)-1,2,3,4-tetrahydroisoquinolin-8-ol obtained in Referential Example 11-(1), in the same manner as described in Referential Example 1 and Example 1-(1).

Optical Rotation: $[\alpha]_D^{25} = -83.0°$ (C=0.684, chloroform)

(2) Preparation of (+) Optical Isomer of Compound 1

The captioned compound was prepared as a colorless oil using (+)-6,7-dimethoxy-1-(4-methoxybenzyl)-1,2,3,4-tetrahydroisoquinolin-8-ol obtained in Referential Example 11-(2), in the same manner as described in Referential Example 1 and Example 1-(1).

Optical Rotation: $[\alpha]_D^{25} = +82.1°$ (C=0.702, chloroform) Compound 75 (Example 75) was prepared using compound 4 obtained in Example 4, in the same manner as described in Example 30.

EXAMPLE 75

Compound 75 appearance: yellow oil

IR(neat, 2932,2854,2776,1650,1611,1584,1518, 1500,1461,1401,1374,1344,1305,1248, 1179,1122,1083,1032,831

High Resolution FAB-MS(m/z, (C31H38N2O6+H)+): Calcd.: 535.2808. Found: 535.2826.

1H-NMR(300 MHz, CDCl3, δ ppm): 2.27+2.28(6H,s×2),2.37–2.60(1H,m),2.67(1H,d, J=15.0 Hz),2.73(1H,dd,J=10.8 Hz,13.7 Hz),2.79–2.98 (1H,m),3.05(1H,dd,J=2.5 Hz,13.7 Hz),3.18–3.36(1H, m),3.42(1H,d,J=15.0 Hz),3.49(2H,s),3.74+3.75(3H,s×2),3.86+3.88(3H,s×-2),3.93(3H,s),4.34(1H,dd+m, J=2.5 Hz,10.5 Hz),4.65–4.74(1H,m),5.06+5.07(1H,d×2,J=10.9 Hz,10.9 Hz),5.16+5.38(1H,d×2,J=10.9 Hz, 10.9 Hz),6.40+6.45(1H,s×2),6.69+6.70(2H,d×2, J=8.6 Hz,8.6 Hz),6.77+6.79(2H,d×2,J=8.6 Hz,8.6 Hz), 7.32–7.55(4H,m)

What is claimed is:

1. A compound represented by formula (I):

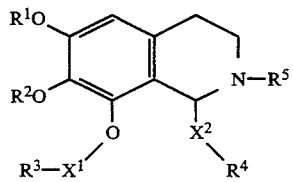

wherein
each of R$^1$ and R$^2$ is independently lower alkyl or both are combined together to form a methylene group;

X$^1$ is a divalent alkylene chain having 1 to 5 carbon atoms which may be substituted with lower alkyl one optional methylene group in which alkylene chain may be replaced by one group selected from the group consisting of oxy, thio, sulfinyl, sulfonyl or a group shown by formula: NR$^6$— wherein R$^6$ is hydrogen atom or lower alkyl; provided that said methylene group is not the methylene group adjacent to the oxygen atom at the 8-position of the isoquinoline ring;

$X^2$ is a divalent alkylene chain having 1 to 4 carbon atoms which may be substituted with lower alkyl;

each of $R^3$ and $R^4$ is independently aryl selected from the group consisting of phenyl and naphthyl each of which is optionally substituted with 1 to 3 substituents which are the same or different and are selected from the group consisting of lower alkyl, lower alkoxy, methylenedioxy, halogen, nitro, hydroxy, cyano, lower alkoxycarbonyl, lower alkanoyl, amino, N-mono-lower alkylamino, N,N-di-lower alkylamino, carbamoyl, N-mono-lower alkylcarbamoyl, N,N-di-lower alkylcarbamoyl, amino-lower alkyl, N-mono-lower alkylamino-lower alkyl, N,N-di-lower alkylamino-lower alkyl, N-(hydroxy-lower alkyl) amino-lower alkyl, N-lower-alkyl-N-(hydroxy-lower alkyl) amino-lower alkyl, N,N-di (hydroxy-lower alkyl) amino-lower alkyl, N-(lower alkoxy-lower alkyl) amino-lower alkyl, N-lower alkyl-N-(lower alkoxy-lower alkyl) amino-lower alkyl, N,N-di(lower alkoxy-lower alkyl) amino-lower alkyl and lower alkyl which is substituted with a group selected from the group consisting of pyrrolidinyl, 1,3-thiazolidinyl, piperidinyl, morpholinyl, thiomorpholinyl, piperazinyl, and S-oxide and N-alkylated derivatives thereof pyridyl and $R^5$ is lower alkoxycarbonyl lower alkylsulfonyl, a group shown by formula:

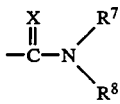

wherein each of $R^7$ and $R^8$ independently is a hydrogen atom or lower alkyl which is optionally substituted with 1 or 2 substituents, which are the same or different and are selected from the group consisting of hydroxy and lower alkoxy and X represents an oxygen atom or a sulfur atom, or $R^5$ is lower alkanoyl which is optionally substituted with 1 or 2 substituents, which are the same or different and are selected from the group consisting of lower alkylsulfinyl, a group shown by formula: $R^9S-$ wherein $R^9$ is a hydrogen atom, lower alkyl, lower alkanoyl, carbamoyl, N-mono-lower alkylcarbonyl, N,N-di-lower alkyl-carbamoyl or lower alkoxycarbonyl; a group shown by formula: $R^{10}O-$ wherein $R^{10}$ represents hydrogen, lower alkyl or lower alkanoyl which are optionally substituted with hydroxy; and a group shown by formula:

wherein each $R^{11}$ and $R^{12}$ independently is hydrogen, lower alkyl or lower alkanoyl, or both are combined together to for pyrrolidino, 2-pyrrolidion-1-yl, morpholino or piperidino, and a pharmaceutically acceptable salt thereof.

2. A compound or a pharmaceutically acceptable salt thereof according to claim 1, wherein each of $R^1$ and $R^2$ is independently lower alkyl or both are combined together to form a methylene group; $R^4$ represents phenyl wherein 1 to 3 hydrogen atoms on the benzene ring may be replaced by 1 to 3 substituents selected from the group consisting of lower alkoxy and methylenedioxy, or pyridyl; $X^2$ represents $CH_2$ or $CH_2CH_2$; $R^3$ is a group represented by formula:

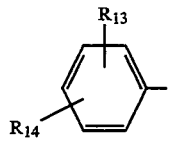

wherein $R^{13}$ is hydrogen atom or lower alkoxy; and $R^{14}$ is amino, N-mono-lower alkylamino or N,N-di-lower alkylamino or a group shown by formula:

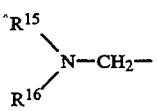

wherein each of $R^{15}$ and $R^{16}$ is independently hydrogen or lower alkyl wherein a hydrogen atom on the carbon atom not adjacent to the nitrogen atom is replaced by hydroxy or lower alkoxy; or both $R^{15}$ and $R^{16}$ are combined together with the nitrogen atom adjacent thereto to form pyrrolidinyl, 1,3-thiazolidinyl, piperidinyl, morpholinyl, thiomorpholinyl, piperazinyl and S-oxide and N-alkylated derivatives thereof; or a pyridyl group.

3. A pharmaceutical composition which comprises a therapeutically effective amount of a compound or pharmaceutically acceptable salt thereof according to claim 1 as active ingredient and a pharmaceutically acceptable dilient, carrier or solvent.

4. A method for the treatment of arrhythmia, which comprises administering to mammal a compound or a pharmaceutically acceptable salt thereof according to claim 1 in a pharmaceutically effective amount.

* * * * *